(12) United States Patent
Bui et al.

(10) Patent No.: US 7,884,158 B2
(45) Date of Patent: Feb. 8, 2011

(54) COSMETIC COMPOSITIONS CONTAINING BLOCK COPOLYMERS, TACKIFIERS AND PHENYLATED SILICONES

(75) Inventors: Hy Si Bui, Piscataway, NJ (US); Shao Xiang Lu, Plainsboro, NJ (US); François Pradier, Paris (FR); Ramon Mercado, Clifton, NJ (US)

(73) Assignee: L'Oréal (FR)

( * ) Notice: Subject to any disclaimer, the term of this patent is extended or adjusted under 35 U.S.C. 154(b) by 813 days.

(21) Appl. No.: 11/219,946

(22) Filed: Sep. 6, 2005

(65) Prior Publication Data

US 2007/0055014 A1 Mar. 8, 2007

(51) Int. Cl.
- *C08L 51/00* (2006.01)
- *A61Q 1/00* (2006.01)
- *A61Q 1/04* (2006.01)
- *A61Q 5/02* (2006.01)

(52) U.S. Cl. .............................. 525/64; 424/63; 424/64; 424/70.11; 424/70.12

(58) Field of Classification Search .................... 525/64
See application file for complete search history.

(56) References Cited

U.S. PATENT DOCUMENTS

| | | | |
|---|---|---|---|
| 2,463,264 A | 3/1949 | Graenacher et al. | |
| 3,148,125 A | 9/1964 | Strianse et al. | |
| 3,645,705 A | 2/1972 | Miller et al. | |
| 3,833,365 A * | 9/1974 | Hiwano et al. ................. | 430/54 |
| 3,937,811 A | 2/1976 | Papantoniou et al. | |
| 4,367,390 A | 1/1983 | Balleys et al. | |
| 4,387,089 A | 6/1983 | De Polo | |
| 4,414,372 A | 11/1983 | Farnham et al. | |
| 4,417,034 A | 11/1983 | Webster | |
| 4,489,057 A | 12/1984 | Welters et al. | |
| 4,508,880 A | 4/1985 | Webster | |
| 4,524,196 A | 6/1985 | Farnham et al. | |
| 4,536,405 A * | 8/1985 | Nara et al. ................... | 514/781 |
| 4,562,067 A | 12/1985 | Hopp et al. | |
| 4,581,428 A | 4/1986 | Farnham et al. | |
| 4,585,597 A | 4/1986 | Lang et al. | |
| 4,588,795 A | 5/1986 | Dicker et al. | |
| 4,598,161 A | 7/1986 | Farnham et al. | |
| 4,605,716 A | 8/1986 | Hertler | |
| 4,622,372 A | 11/1986 | Dicker et al. | |
| 4,655,768 A * | 4/1987 | Marecki et al. .............. | 424/448 |
| 4,656,233 A | 4/1987 | Hertler et al. | |
| 4,681,918 A | 7/1987 | Webster | |
| 4,693,929 A * | 9/1987 | Ryoke et al. ................. | 428/323 |
| 4,693,935 A | 9/1987 | Mazurek | |
| 4,711,942 A | 12/1987 | Webster | |
| 4,822,859 A | 4/1989 | Sogah | |
| 4,972,037 A | 11/1990 | Garbe | |
| 4,980,167 A * | 12/1990 | Harashima et al. .......... | 424/401 |
| 4,981,902 A | 1/1991 | Mitra et al. | |
| 4,981,903 A | 1/1991 | Garbe et al. | |
| 4,985,459 A | 1/1991 | Sunshine et al. | |
| 5,061,481 A | 10/1991 | Suzuki et al. | |
| 5,073,372 A | 12/1991 | Turner et al. | |
| 5,087,445 A | 2/1992 | Haffey et al. | |
| 5,166,355 A | 11/1992 | Leistner et al. | |
| 5,209,924 A | 5/1993 | Garbe et al. | |
| 5,214,093 A * | 5/1993 | Nell et al. .................... | 524/506 |
| 5,219,560 A | 6/1993 | Suzuki et al. | |
| 5,233,040 A | 8/1993 | Raspanti | |
| 5,237,071 A | 8/1993 | Leistner et al. | |
| 5,262,087 A | 11/1993 | Tachibana et al. | |
| 5,294,438 A | 3/1994 | Chang et al. | |
| 5,346,691 A | 9/1994 | Raspanti | |
| 5,378,271 A * | 1/1995 | Arimoto et al. .............. | 106/236 |
| 5,468,477 A | 11/1995 | Kumar et al. | |
| 5,498,666 A * | 3/1996 | Nambu et al. ................ | 525/100 |
| 5,500,209 A | 3/1996 | Mendolia et al. | |
| 5,512,931 A * | 4/1996 | Nakajima et al. ............ | 347/213 |
| 5,585,091 A | 12/1996 | Pelzer et al. | |
| 5,603,948 A * | 2/1997 | Merkle et al. ................ | 424/448 |
| 5,783,657 A | 7/1998 | Pavlin et al. | |
| 5,801,244 A | 9/1998 | Raspanti | |
| 5,849,275 A | 12/1998 | Calello et al. | |
| 5,851,517 A * | 12/1998 | Mougin et al. ............ | 424/78.02 |
| 5,866,149 A | 2/1999 | Piot et al. | |
| 5,874,069 A | 2/1999 | Mendolia et al. | |
| 5,919,441 A | 7/1999 | Mendolia et al. | |

(Continued)

FOREIGN PATENT DOCUMENTS

| | | |
|---|---|---|
| DE | 197 26 184 | 12/1998 |
| EP | 114607 | 8/1984 |
| EP | 517104 | 12/1992 |
| EP | 570838 | 11/1993 |
| EP | 669323 | 8/1995 |
| EP | 775698 | 5/1997 |
| EP | 796851 | 9/1997 |
| EP | 863145 | 9/1998 |
| EP | 878469 | 11/1998 |
| EP | 893119 | 1/1999 |

(Continued)

OTHER PUBLICATIONS

"Handbook of Pressure Sensitive Adhesive Technology" 3rd Edition, D. Satas, 1999.
"*Solubility Parameter Values*" by Eric A. Grulke in the work "*Polymer Handbook*" 3rd edition (1989), Chapter VII, pp. 519-559.
C. M. Hansen: "*The three-dimensional solubility parameters*" J. Paint Technol, 39, 105(1967).
Chapter VIII of *Cosmetics and Science and Technology* (1957) by Segarin et al., pp. 189-212.
*International Cosmetic Ingredient Dictionary and Handbook* (9th ed. 2002).

*Primary Examiner*—Randy Gulakowski
*Assistant Examiner*—Robert Loewe
(74) *Attorney, Agent, or Firm*—Lerner, David, Littenberg, Krumholz & Mentlik, LLP

(57) ABSTRACT

A cosmetic composition containing at least one block copolymer having a hard segment and a soft segment, at least one tackifier component, at least one phenylated silicone, at least one solvent, and optionally, at least one colorant.

23 Claims, No Drawings

U.S. PATENT DOCUMENTS

| | | | |
|---|---|---|---|
| 5,945,095 A * | 8/1999 | Mougin et al. | 424/78.02 |
| 5,955,060 A | 9/1999 | Huglin et al. | |
| 5,962,452 A | 10/1999 | Haase et al. | |
| 5,976,512 A | 11/1999 | Huber | |
| 5,981,680 A | 11/1999 | Petroff et al. | |
| 5,998,570 A | 12/1999 | Pavlin et al. | |
| 6,018,044 A | 1/2000 | Huber | |
| 6,033,650 A | 3/2000 | Calello et al. | |
| 6,051,216 A | 4/2000 | Barr et al. | |
| 6,066,313 A | 5/2000 | Anton et al. | |
| 6,074,054 A | 6/2000 | Katsuyama | |
| 6,231,885 B1 * | 5/2001 | Carrara | 424/448 |
| 6,235,271 B1 | 5/2001 | Luther et al. | |
| 6,254,876 B1 * | 7/2001 | de la Poterie et al. | 424/401 |
| 6,264,934 B1 | 7/2001 | Kantner et al. | |
| 6,277,358 B1 | 8/2001 | Calello et al. | |
| 6,288,199 B1 | 9/2001 | Ambrose et al. | |
| 6,403,070 B1 | 6/2002 | Pataut et al. | |
| 6,406,502 B1 | 6/2002 | Audousset | |
| 6,423,306 B2 | 7/2002 | Caes et al. | |
| 6,448,303 B1 * | 9/2002 | Paul | 523/105 |
| 6,464,967 B1 | 10/2002 | Collin | |
| 6,468,678 B1 * | 10/2002 | Dahlin et al. | 428/800 |
| 6,517,818 B1 * | 2/2003 | Golz-Berner et al. | 424/64 |
| 6,562,888 B1 * | 5/2003 | Frihart et al. | 524/274 |
| 6,656,458 B1 | 12/2003 | Philippe et al. | |
| 6,685,925 B2 * | 2/2004 | Frechet et al. | 424/70.16 |
| 6,737,048 B2 * | 5/2004 | Abend et al. | 424/65 |
| 6,780,402 B1 | 8/2004 | Agostini et al. | |
| 6,811,770 B2 * | 11/2004 | Ferrari et al. | 424/64 |
| 2001/0007654 A1 * | 7/2001 | Caes et al. | 424/70.11 |
| 2002/0055562 A1 * | 5/2002 | Butuc | 524/80 |
| 2002/0110573 A1 * | 8/2002 | Caes et al. | 424/401 |
| 2002/0128345 A1 * | 9/2002 | Paul | 523/112 |
| 2002/0160026 A1 * | 10/2002 | Frechet et al. | 424/401 |
| 2003/0108498 A1 * | 6/2003 | Stephens et al. | 424/63 |
| 2003/0113283 A1 * | 6/2003 | Mattai et al. | 424/65 |
| 2003/0161798 A1 * | 8/2003 | Kellner et al. | 424/64 |
| 2003/0161800 A1 * | 8/2003 | Guenin et al. | 424/65 |
| 2003/0236387 A1 | 12/2003 | Pavlin | 528/272 |
| 2004/0052746 A1 * | 3/2004 | Tamareselvy et al. | 424/70.11 |
| 2004/0151680 A1 * | 8/2004 | Patil et al. | 424/70.12 |
| 2004/0170586 A1 * | 9/2004 | Ferrari et al. | 424/63 |
| 2005/0095213 A1 * | 5/2005 | Blin et al. | 424/70.11 |
| 2005/0172421 A1 * | 8/2005 | Jager-Lezer et al. | 8/405 |
| 2006/0127341 A1 * | 6/2006 | Lion et al. | 424/70.16 |
| 2007/0014745 A1 * | 1/2007 | Arnaud et al. | 424/70.11 |

FOREIGN PATENT DOCUMENTS

| | | |
|---|---|---|
| EP | 933376 | 8/1999 |
| FR | 3937811 | 1/1975 |
| FR | 2326405 | 4/1977 |
| FR | 2440933 | 6/1980 |
| WO | WO-93/04665 | 3/1993 |
| WO | WO-93/23446 | 11/1993 |
| WO | WO-95/06078 | 3/1995 |
| WO | WO-95/15741 | 6/1995 |
| WO | WO-01/32727 | 5/2001 |
| WO | WO-01/32737 | 5/2001 |
| WO | WO 2004/055082 * | 7/2004 |

* cited by examiner

COSMETIC COMPOSITIONS CONTAINING BLOCK COPOLYMERS, TACKIFIERS AND PHENYLATED SILICONES

BACKGROUND OF THE INVENTION

There have been many developments in connection with improving comfort, wear, shine and/or longevity of cosmetic compositions for the face, eye, lips nails or hair. For example, U.S. Pat. No. 6,074,054 is directed to a composition for application to the lips comprising silicone resins and dimethicone gums of high viscosity. U.S. Pat. No. 6,277,358 teaches a cosmetic composition with good wear properties comprising film formers capable of being cross linked, a cross linking agent and ways to control the cross linking reaction. U.S. Pat. No. 6,464,967 teaches the use of specific polyolefin waxes in mascara and eyebrow compositions to improve application, comfort and wear. U.S. Pat. No. 6,423,306 discloses transfer free compositions with block copolymers and additional film formers. U.S. Pat. No. 6,780,402 discloses cosmetic compositions containing phenylated silicone oils and volatile solvents. Mixtures of waxes have been used to combine properties such as film hardness and adhesion to the lash. See, e.g. WO95/15741.

BRIEF SUMMARY OF THE INVENTION

A first aspect of the present invention is directed to a cosmetic composition comprising:
a) at least one block copolymer having a hard block segment and a soft block segment;
b) at least one tackifier component;
c) at least one phenylated silicone compound;
d) at least one solvent; and
e) optionally, at least one colorant.

A second aspect of the present invention is directed to a method of treating a keratinous substrate by contacting the substrate with the above-disclosed cosmetic composition.

DETAILED DESCRIPTION OF THE INVENTION

Other than in the operating examples, or where otherwise indicated, all numbers expressing quantities of ingredients and/or reaction conditions are to be understood as being modified in all instances by the term "about."

Block Copolymer

The block copolymers of the present invention are characterized by the presence of at least one "hard" segment, and at least one "soft" segment. Aside from their compositional nature, the hard and soft segments of the block copolymers of the present invention are defined in terms of their respective glass transition temperatures, "$T_g$". More particularly, the hard segment has a $T_g$ of 50° C. or more, whereas the soft segment has a $T_g$ of 0° C. or less. The glass transition temperature $T_g$ for the hard block can range from 50° C. to 150° C.; 60° C. to 125° C.; 70° C. to 120° C.; 80° C. to 110° C. The glass transition temperature $T_g$ for the soft segment of the block copolymer can range from 0° C. to −150° C.; −10° C. to −125° C.; −25 to −100° C. A more in depth explanation can be found in U.S. Pat. Nos. 5,294,438 and 6,403,070, the entire contents of which are hereby incorporated by reference.

One type of block copolymer which may be employed by the present invention is a thermoplastic elastomer. The hard segments of the thermoplastic elastomer typically comprise vinyl monomers in varying amounts. Examples of suitable vinyl monomers include, but are not limited to, styrene, methacrylate, acrylate, vinyl ester, vinyl ether, vinyl acetate, and the like.

The soft segments of the thermoplastic elastomer comprise olefin polymers and/or copolymers which may be saturated, unsaturated, or combinations thereof. Suitable olefin copolymers may include, but are not limited to, ethylene/propylene copolymers, ethylene/butylene copolymers, propylene/butylene copolymers, polybutylene, polyisoprene, polymers of hydrogenated butanes and isoprenes, and mixtures thereof.

Thermoplastic elastomers useful in the present invention are block copolymers e.g., di-block, tri-block, multi-block, radial and star block copolymers, and mixtures and blends thereof. A di-block thermoplastic elastomer is usually defined as an A-B type or a hard segment (A) followed by a soft segment (B) in sequence. A tri-block is usually defined as an A-B-A type copolymer or a ratio of one hard, one soft, and one hard segment. Multi-block or radial block or star block thermoplastic elastomers usually contain any combination of hard and soft segments, provided that the elastomers possess both hard and soft characteristics.

In some embodiments, the thermoplastic elastomer of the present invention may be chosen from the class of Kraton™ rubbers (Shell Chemical Company) or from similar thermoplastic elastomers. Kraton™ rubbers are thermoplastic elastomers in which the polymer chains comprise a di-block, tri-block, multi-block or radial or star block configuration or numerous mixtures thereof. The Kraton™ tri-block rubbers have polystyrene (hard) segments on each end of a rubber (soft) segment, while the Kraton™ di-block rubbers have a polystyrene (hard) segment attached to a rubber (soft) segment. The Kraton™ radial or star configuration may be a four-point or other multipoint star made of rubber with a polystyrene segment attached to each end of a rubber segment. The configuration of each of the Kraton™ rubbers forms separate polystyrene and rubber domains.

Each molecule of Kraton™ rubber is said to comprise block segments of styrene monomer units and rubber monomer and/or co-monomer units. The most common structure for the Kraton™ triblock copolymer is the linear A-B-A block type styrene-butadiene-styrene, styrene-isoprene-styrene, styrene-ethylenepropylene-styrene, or styrene-ethylenebutylene-styrene. The Kraton™ di-block is preferably the AB block type such as styrene-ethylenepropylene, styrene-ethylenebutylene, styrene-butadiene, or styrene-isoprene. The Kraton™ rubber configuration is well known in the art and any block copolymer elastomer with a similar configuration is within the practice of the invention. Other block copolymers are sold under the tradename Septon (which represent elastomers known as SEEPS, sold by Kurary, Co., Ltd) and those sold by Exxon Dow under the tradename Vector™.

Other thermoplastic elastomers useful in the present invention include those block copolymer elastomers comprising a styrene-butylene/ethylene-styrene copolymer (tri-block), an ethylene/propylene-styrene copolymer (radial or star block) or a mixture or blend of the two. (Some manufacturers refer to block copolymers as hydrogenated block copolymers, e.g. hydrogenated styrene-butylene/ethylene-styrene copolymer (tri-block).

The thermoplastic elastomers according to the invention may be chosen from adhesives of "pressure-sensitive adhesive" type for example, such as those mentioned in the "Handbook of Pressure Sensitive Adhesive Technology" 3rd Edition, D. Satas, the entire contents of which is hereby incorporated by reference. The thermoplastic elastomers according to the invention may also be adhesive polymers chosen from polyurethanes, ethylene/vinyl acetate polymers, and blends thereof.

The thermoplastic elastomers of the present invention may be employed in gelled form. By the term "gelled," it is meant that the block copolymer is dissolved in a solvent. The block copolymer is formulated by dissolving it in a solvent such as oils, hydrocarbon solvents and esters. Hydrocarbons useful in the practice of the invention include but are not limited to mineral oils, mineral solvents, mineral spirits, petroleum, waxes, synthetic hydrocarbons, animal oils, vegetable oils, and mixtures thereof. In some embodiments, the block copolymer is formulated by dissolving the block copolymer in isododecane or a light paraffinic solvent. Specific examples of thermoplastic elastomers in gelled form include, but are not limited to, Versagel M5960 and Versagel M5970, commercially available from Penreco of Houston Tex., as well as those from Brooks Industries, such as Gel Base (e.g., Code 05895, which is a styrene-ethylene/propylene mixed block copolymer already in combination with a solvent, namely isododecane).

The thermoplastic elastomer may be formed by dissolving a block copolymer in a non-hydrocarbon solvent such as amyl acetate, butyl acetate, isobutyl acetate, ethyl acetate, propyl acetate or isopropyl acetate. The solvent and solubility conditions for formulating a block copolymer film former from a block copolymer will be chosen by a person skilled in the art in order to prepare a composition which has the desired properties. One of ordinary skill in the art will be able to determine the solubility parameters and choose a solvent based on the block copolymer chosen for the envisaged application. More information regarding solubility parameters and solvents useful in the processing of specific block copolymers is available from the various manufacturers of block copolymers, e.g., Shell Chemical Company. Additional discussions of polymer solubility parameter concepts are presented in: *Encyclopedia of Polymer Science and Technology*, Vol. 3, Interscience, New York (1965) and *Encyclopedia of Chemical Technology*, Supp. Vol., Interscience, New York (1971).

In some embodiments, the thermoplastic elastomer is a tri-block rubber elastomer. The tri-block rubber elastomer can be styrene ethylene/butylene tri-block copolymers. Representative examples of styrene ethylene/butylene tri-block copolymers are KRATON G polymers, e.g. KRATON G1657M, commercially available from Shell.

The amounts of the block (co)polymer or (co)polymers, as well as their structure (di-block, tri-block, etc.), affect the nature of the thermoplastic elastomer, including its gelled form, which may range from fragile to soft/flexible to firm. For instance, soft gels contain relatively high amounts of soft segments, and firm gels contain relatively high amounts of hard segments. The overall properties of the composition may also be affected by including more than one such block copolymer e.g., including a mixture of copolymers. For example, the presence of tri-block copolymers enhances the integrity of the film formed. The gel may also be transparent, translucent or opaque, depending upon the other cosmetically acceptable ingredients added, as described herein.

The at least one block copolymer may also be chosen from a polyamide comprising a polymer skeleton comprising at least one amide repeating unit and optionally at least one pendant fatty chain and/or at least one terminal chain that are optionally functionalized and comprise from 8 to 120 carbon atoms, bonded to at least one of the amide repeating units via at least one linking group. The pendant fatty chains may be linked to at least one of the nitrogen atoms in the amide repeating units.

The polyamide polymer may have a weight-average molecular mass of less than 100,000, such as less than 50,000. In another embodiment, the weight-average molecular mass may range from 1,000 to 30,000, such as from 2,000 to 20,000, further such as from 2,000 to 10,000.

A polyamide polymer may comprise, for example, a polymer skeleton which comprises at least one amide repeating unit, i.e., a polyamide skeleton. In one embodiment, the polyamide skeleton may further comprise at least one terminal fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group, and/or at least one pendant fatty chain chosen from alkyl chains, for example, alkyl chains comprising at least four carbon atoms, and alkenyl chains, for example, alkenyl chains comprising at least four carbon atoms, bonded to the at least one polyamide skeleton via at least one linking group. In one embodiment, the polyamide skeleton may comprise at least one terminal fatty chain chosen from fatty chains comprising 8 to 120 carbon atoms, such as, for example, 12 to 68 carbon atoms, bonded to the at least one polyamide skeleton via at least one linking group and/or at least one pendant fatty chain chosen from fatty chains comprising 8 to 120 carbon atoms, such as, for example, 12 to 68 carbon atoms, bonded to the at least one polyamide skeleton via at least one linking group, such as bonded to any carbon or nitrogen of the polyamide skeleton via the at least one linking group. In one embodiment, the at least one linking group is chosen from single bonds and urea, urethane, thiourea, thiourethane, thioether, thioester, ester, ether and amine groups. For example, the at least one linking group is chosen from ureas, esters, and amines, and as a further example, is chosen from esters and amines. The bond is, for example, an ester bond. In one embodiment, these polymers comprise a fatty chain at each end of the polymer skeleton, such as the polyamide skeleton.

In one embodiment, due to the presence of at least one chain, the polyamide polymers may be readily soluble in oils (i.e., water-immiscible liquid compounds) and thus may give macroscopically homogeneous compositions even with a high content (at least 25%) of the polyamide polymers, unlike certain polymers of the prior art that do not contain such alkyl or alkenyl chains at the end of the polyamide skeleton. As defined herein, a composition is soluble if it has a solubility of greater than 0.01 g per 100 ml of solution at 25° C.

In a further embodiment, the polyamide polymers can be chosen from polymers resulting from at least one polycondensation reaction between at least one acid chosen from dicarboxylic acids comprising at least 32 carbon atoms, such as 32 to 44 carbon atoms, and at least one amine chosen from diamines comprising at least 2 carbon atoms, such as from 2 to 36 carbon atoms, and triamines comprising at least 2 carbon atoms, such as from 2 to 36 carbon atoms. The dicarboxylic acids can, for example, be chosen from dimers of at least one fatty acid comprising at least 16 carbon atoms, such as oleic acid, linoleic acid and linolenic acid. The at least one amine can, for example, be chosen from diamines, such as ethylenediamine, hexylenediamine, hexamethylenediamine, phenylenediamine and triamines, such as ethylenetriamine.

The polyamide polymers may also be chosen from polymers comprising at least one terminal carboxylic acid group. The at least one terminal carboxylic acid group can, for example, be esterified with at least one alcohol chosen from monoalcohols comprising at least 4 carbon atoms. For example, the at least one alcohol can be chosen from monoalcohols comprising from 10 to 36 carbon atoms. In a further embodiment, the monoalcohols can comprise from 12 to 24 carbon atoms, such as from 16 to 24 carbon atoms, and for example 18 carbon atoms.

In one embodiment, the polyamide polymer may be chosen from those described in U.S. Pat. No. 5,783,657, the disclosure of which is incorporated herein by reference, which are polymers of the following structural formula:

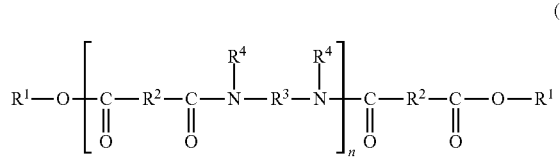

in which:

n is an integer which represents the number of amide units such that the number of ester groups present in said at least one polyamide polymer ranges from 10% to 50% of the total number of all said ester groups and all said amide groups comprised in said at least one polyamide polymer;

$R^1$, which are identical or different, are each chosen from alkyl groups comprising at least 4 carbon atoms and alkenyl groups comprising at least 4 carbon atoms. In one embodiment, the alkyl group comprises from 4 to 24 carbon atoms and the alkenyl group comprises from 4 to 24 carbon atoms;

$R^2$, which are identical or different, are each chosen from $C_4$ to $C_{42}$ hydrocarbon-based groups with the proviso that at least 50% of all $R^2$ are chosen from $C_{30}$ to $C_{42}$ hydrocarbon-based groups;

$R^3$, which are identical or different, are each chosen from organic groups comprising atoms chosen from carbon atoms, hydrogen atoms, oxygen atoms and nitrogen atoms with the proviso that $R^3$ comprises at least 2 carbon atoms; and $R^4$, which are identical or different, are each chosen from hydrogen atoms, $C_1$ to $C_{10}$ alkyl groups and a direct bond to at least one group chosen from $R^3$ and another $R^4$ such that when said at least one group is chosen from another $R^4$, the nitrogen atom to which both $R^3$ and $R^4$ are bonded forms part of a heterocyclic structure defined in part by $R^4$—N—$R^3$, with the proviso that at least 50% of all $R^4$ are chosen from hydrogen atoms.

In one embodiment, the at least one terminal fatty chain of formula (I) is linked to the last hetero atom, in this case nitrogen, of the polyamide skeleton. In a further embodiment, the terminal chains are functionalized. In another embodiment, the ester groups of formula (I), are linked to the terminal and/or pendant fatty chains, represent from 15% to 40% of the total number of ester and amide groups, such as, for example, from 20% to 35%.

In one embodiment, n may be an integer ranging from 1 to 5, for example, an integer ranging from 3 to 5. In the present invention, $R^1$, which are identical or different, can, for example, each be chosen from $C_{12}$ to $C_{22}$ alkyl groups, such as from $C_{16}$ to $C_{22}$ alkyl groups.

$R^2$, which are identical or different, can, for example, each be chosen from $C_{10}$ to $C_{42}$ alkyl groups. At least 50% of all $R^2$, which are identical or different, can, for example, each be chosen from groups comprising from 30 to 42 carbon atoms. At least 75% of all $R^2$, which are identical or different, can, for example, each be chosen from groups comprising from 30 to 42 carbon atoms. In the two aforementioned embodiments, the remaining $R^2$, which are identical or different, can, for example, each be chosen from $C_4$ to $C_{19}$ groups, such as $C_4$ to $C_{12}$ groups.

$R^3$, which can be identical or different, can, for example, each be chosen from $C_2$ to $C_{36}$ hydrocarbon-based groups and polyoxyalkylene groups. In another example, $R^3$, which can be identical or different, can each, for example, be chosen from $C_2$ to $C_{12}$ hydrocarbon-based groups. In another embodiment, $R^4$, which can be identical or different, can each be chosen from hydrogen atoms. As used herein, hydrocarbon-based groups may be chosen from linear, cyclic and branched, and saturated and unsaturated groups. The hydrocarbon-based groups can be chosen from aliphatic and aromatic groups. In one example, the hydrocarbon-based groups are chosen from aliphatic groups. The alkyl and alkylene groups may be chosen from linear, cyclic and branched, and saturated and unsaturated groups.

In general, the pendant and terminal fatty chains may be chosen from linear, cyclic and branched, and saturated and unsaturated groups. The pendant and terminal fatty chains can be chosen from aliphatic and aromatic groups. In one example, the pendant and terminal fatty chains are chosen from aliphatic groups.

The polyamide polymer of formula (I) may, for example, be in the form of a mixture of polymers, and this mixture may also comprise a compound of formula (I) wherein n is equal to zero, i.e., a diester.

Non-limiting examples of polyamide polymers which may be used in the composition according to the present invention include the commercial products sold by Arizona Chemical under the names Uniclear 80 and Uniclear 100. These are sold, respectively, in the form of an 80% (in terms of active material) gel in a mineral oil and a 100% (in terms of active material) gel. These polymers have a softening point ranging from 88° C. to 94° C., and may be mixtures of copolymers derived from monomers of (i) $C_{36}$ diacids and (ii) ethylenediamine, and have a weight-average molecular mass of about 6,000. Terminal ester groups result from esterification of the remaining acid end groups with at least one alcohol chosen from cetyl alcohol and stearyl alcohol. A mixture of cetyl and stearyl alcohols is sometimes called cetylstearyl alcohol.

Other non-limiting examples of at least one polyamide polymer which may be used in the composition according to the present invention include polyamide polymers resulting from the condensation of at least one aliphatic dicarboxylic acid and at least one diamine, the carbonyl and amine groups being condensed via an amide bond. Examples of these polyamide polymers are those sold under the brand name Versamid by the companies General Mills Inc. and Henkel Corp. (Versamid 930, 744 or 1655) or by the company Olin Mathieson Chemical Corp. under the brand name Onamid, in particular Onamid S or C. These resins have a weight-average molecular mass ranging from 6,000 to 9,000. For further information regarding these polyamides, reference may be made to U.S. Pat. Nos. 3,645,705 and 3,148,125, the disclosures of which are hereby incorporated by reference.

Other examples of polyamides include those sold by the company Arizona Chemical under the references Uni-Rez (2658, 2931, 2970, 2621, 2613, 2624, 2665, 1554, 2623 and 2662) and the product sold under the reference Macromelt 6212 by the company Henkel. For further information regarding these polyamides, reference may be made to U.S. Pat. No. 5,500,209, the disclosure of which is hereby incorporated by reference. Such polyamides display high melt viscosity characteristics. MACROMELT 6212, for example, has a high melt viscosity at 190° C. of 30-40 poise (as measured by a Brookfield Viscometer, Model RVF #3 spindle, 20 RPM).

In a further embodiment, the polyamide polymer may be chosen from polyamide resins from vegetable sources. Polyamide resins from vegetable sources may be chosen from, for example, the polyamide resins of U.S. Pat. Nos. 5,783,657 and 5,998,570, the disclosures of which are herein incorporated by reference.

Suitable block copolymers for use in the present invention also include polymers of the polyorganosiloxane type such as those described in documents U.S. Pat. No. 5,874,069, U.S. Pat. No. 5,919,441, U.S. Pat. No. 6,051,216 and U.S. Pat. No. 5,981,680, the entire contents of which are hereby incorporated by reference.

These block copolymers may belong to the following two families:

polyorganosiloxanes comprising at least two groups capable of establishing hydrogen interactions, these two groups being located in the polymer chain; and/or polyorganosiloxanes comprising at least two groups capable of establishing hydrogen interactions, these two groups being located on grafts or branches.

They are solids that may be dissolved beforehand in a solvent with hydrogen interaction capable of breaking the hydrogen interactions of the polymers, for instance $C_2$ to $C_8$ lower alcohols and especially ethanol, n-propanol or isopropanol, before being placed in the presence of the silicone oils according to the invention. It is also possible to use these hydrogen interaction "breaking" solvents as co-solvents. These solvents may then be stored in the composition or may be removed by selective evaporation, which is well known to those skilled in the art.

The polymers comprising two groups capable of establishing hydrogen interactions in the polymer chain may be polymers comprising at least one moiety corresponding to the formula:

$$\left\{\left[\begin{array}{c}R^1\\|\\Si-O\\|\\R^3\end{array}\right]\left[\begin{array}{c}R^2\\|\\Si-X-G-Y-G-X\\|\\R^4\end{array}\right]_m\right\}_n \quad (I)$$

in which:

1) $R^1$, $R^2$, $R^3$ and $R^4$, which may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms: fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

$$R^5-T{\Large\langle}$$

in which:

T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and $R^5$ represents a linear or branched $C_1$ to $C_{50}$ alkyl group or a polyorganosiloxane chain, possibly comprising one or more ester, amide, urethane, thiocarbamate, urea, thiourea and/or sulphonamide groups, which may be linked to another chain of the polymer;

5) the groups G, which may be identical or different, represent divalent groups chosen from:

$$-\underset{\underset{O}{\|}}{C}-O-; \quad -O-\underset{\underset{O}{\|}}{C}-; \quad -N(R^6)-\underset{\underset{O}{\|}}{C}-;$$

$$-\underset{\underset{O}{\|}}{C}-N(R^6)-; \quad -N(R^6)-SO_2-;$$

$$-SO_2-N(R^6)-; \quad -N(R^6)-\underset{\underset{O}{\|}}{C}-O-;$$

$$-O-\underset{\underset{O}{\|}}{C}-N(R^6)-; \quad -N(R^6)-\underset{\underset{S}{\|}}{C}-O-;$$

$$-O-\underset{\underset{S}{\|}}{C}-N(R^6)-; \quad -N(R^6)-\underset{\underset{O}{\|}}{C}-N(R^6)- \quad \text{and}$$

$$-N(R^6)-\underset{\underset{S}{\|}}{C}-N(R^6)-$$

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

$$-O-\underset{\underset{O}{\|}}{C}- \quad \text{and} \quad -\underset{\underset{O}{\|}}{C}-O-;$$

6) n is an integer ranging from 2 to 500 and preferably from 2 to 200, and m is an integer ranging from 1 to 1 000, preferably from 1 to 700 and better still from 6 to 200.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) $C_{30}$ to $C_{56}$ branched alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

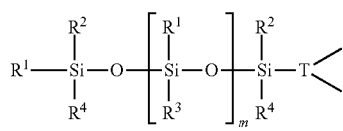

in which $R^1$, $R^2$, $R^3$, $R^4$, T and m are as defined above, and h) polyorganosiloxane chains of formula:

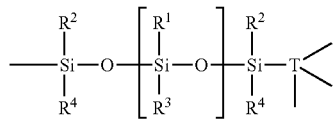

The polyorganosiloxanes of the second family may be polymers comprising at least one moiety corresponding to formula (II):

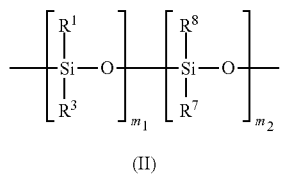

Formula II (II)

in which $R^1$ and $R^3$, which may be identical or different, are as defined above for formula (I), $R^7$ represents a group as defined above for $R^1$ and $R^3$, or represents a group of formula —X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer ranging from 1 to 998, and $m_2$ is an integer ranging from 2 to 500.

According to the invention, the polymer used as gelling agent may be a homopolymer, that is to say a polymer comprising several identical moieties, in particular moieties of formula (I) or of formula (II).

According to the invention, it is also possible to use a polymer consisting of a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to one variant of the invention, it is also possible to use a copolymer furthermore comprising at least one hydrocarbon-based moiety comprising two groups capable of establishing hydrogen interactions, chosen from ester, amide, sulphonamide, carbamate, thiocarbamate, urea and thiourea groups, and combinations thereof.

These copolymers may be block copolymers or grafted copolymers.

According to one embodiment of the invention, the groups capable of establishing hydrogen interactions are amide groups of formulae —C(O)NH— and —HN—C(O)—.

In this case, the polyorganosiloxane may be a polymer comprising at least one moiety of formula (III) or (IV):

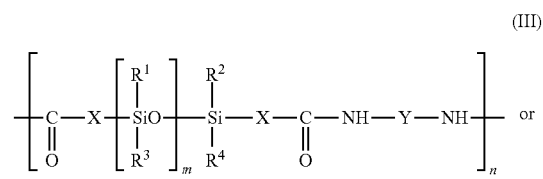

(III)

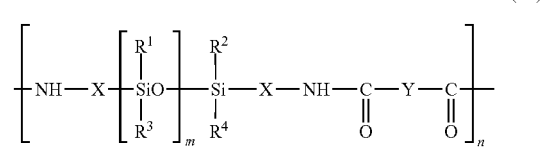

(IV)

in which $R^1$, $R^2$, $R^3$, $R^4$, X, Y, m and n are as defined above.

Such a moiety may be obtained:

either by a condensation reaction between a silicone containing α,ω-carboxylic acid ends and one or more diamines, according to the following reaction scheme:

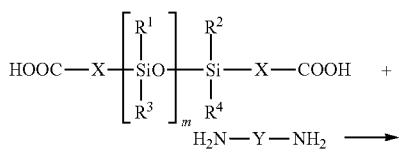

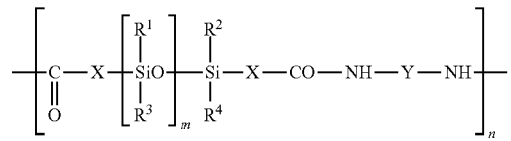

or by reaction of two molecules of α-unsaturated carboxylic acid with a diamine according to the following reaction scheme:

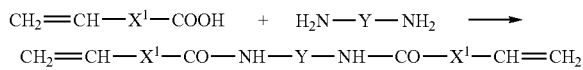

followed by the addition of a siloxane to the ethylenic unsaturations, according to the following scheme:

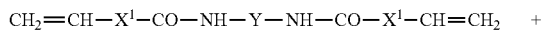

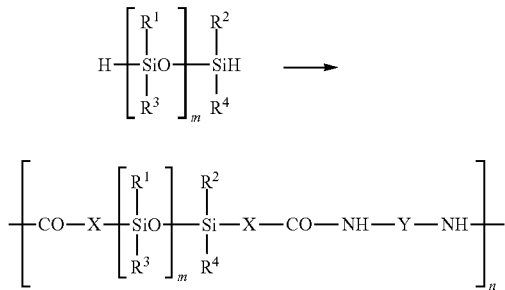

in which $X^1$—$(CH_2)_2$— corresponds to X defined above and Y, $R^1$, $R^2$, $R^3$, $R^4$ and m are as defined above;

or by reaction of a silicone containing $\alpha,\omega$-$NH_2$ ends and a diacid of formula HOOC—Y—COOH according to the following reaction scheme:

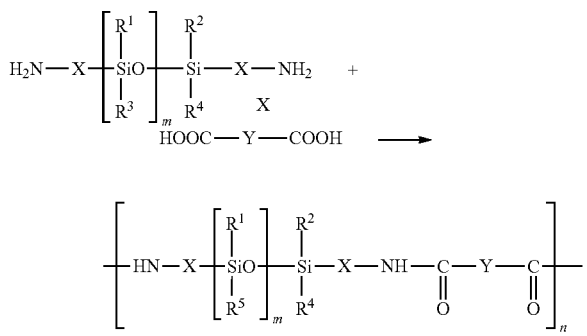

In these polyamides of formula (III) or (IV), m is preferably in the range from 1 to 700, more preferably from 15 to 500 and better still from 15 to 45, and n is in particular in the range from 1 to 500, preferably from 1 to 100 and better still from 4 to 25, X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following elements:

1) 1 to 5 amide, urea or carbamate groups, 2) a $C_5$ or $C_6$ cycloalkyl group, and 3) a phenylene group optionally substituted with 1 to 3 identical or different $C_1$ to $C_3$ alkyl groups.

In formulae (III) and (IV), the alkylene groups may also be substituted with at least one element chosen from the group consisting of:
- a hydroxyl group,
- a $C_3$ to $C_8$ cycloalkyl group,
- one to three $C_1$ to $C_{40}$ alkyl groups,
- a phenyl group optionally substituted with one to three $C_1$ to $C_3$ alkyl groups,
- a $C_1$ to $C_3$ hydroxyalkyl group, and
- a $C_1$ to $C_6$ aminoalkyl group.

In these formulae (III) and (IV), Y may also represent:

in which $R^5$ represents a polyorganosiloxane chain and T represents a group of formula:

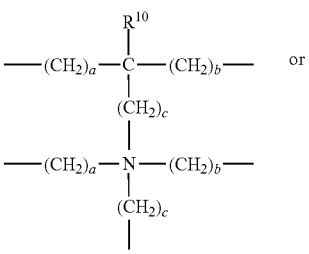

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

(V)

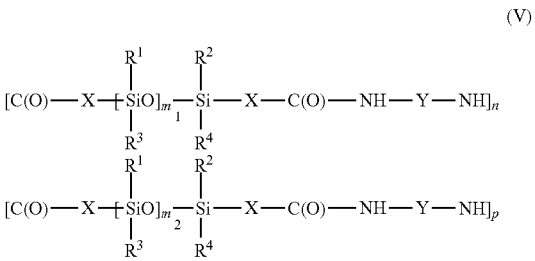

in which X, Y, n and $R^1$ to $R^4$ have the meanings given above, $m_1$ and $m_2$, which are different, are chosen in the range from 1 to 1,000, and p is an integer ranging from 2 to 300.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

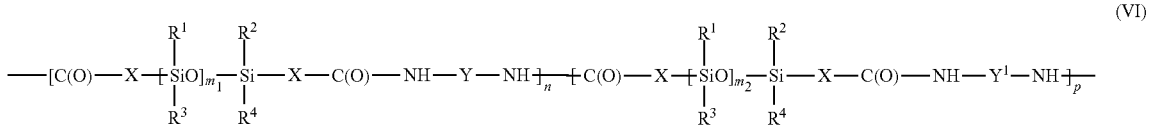

in which $R^1$ to $R^4$, X, Y, $m_1$, $m_2$, n and p have the meanings given above and $Y^1$ is different from Y but chosen from the groups defined for Y. As previously, the various moieties may be structured to form either a block copolymer, or a random copolymer or an alternating copolymer.

In another embodiment of the invention, the polyorganosiloxane may also consist of a grafted copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

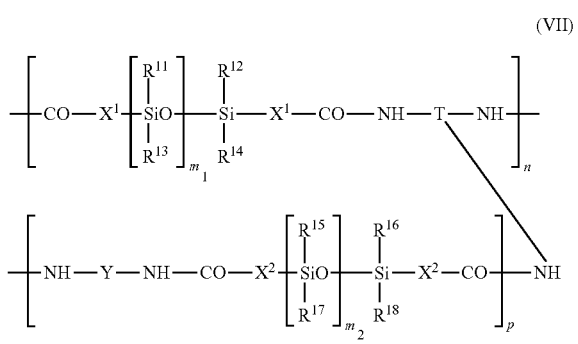

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1,000, and p is an integer ranging from 2 to 500.

In formula (VII), it is preferred that:

p is in the range from 1 to 25 and better still from 1 to 7, $R^{11}$ to $R^{18}$ are methyl groups, T corresponds to one of the following formulae:

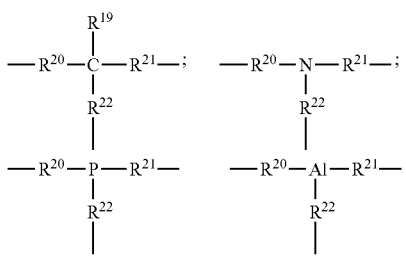

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

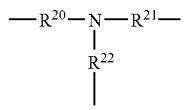

in particular with $R^{20}$, $R^{21}$ and $R^{22}$ representing —$CH_2$—$CH_2$—, $m_1$ and $m_2$ are in the range from 15 to 500 and better still from 15 to 45, $X^1$ and $X^2$ represent —$(CH_2)_{10}$—, and Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:

polyamides of formula (III) in which m is from 15 to 50;

mixtures of two or more polyamides in which at least one polyamide has a value of m in the range from 15 to 50 and at least one polyamide has a value of m in the range from 30 to 50;

polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1 to 99% by weight of the total weight of the polyamide;

mixtures of polyamide of formula (III) combining 1) 80% to 99% by weight of a polyamide in which n is equal to 2 to 10 and in particular 3 to 6, and 2) 1% to 20% of a polyamide in which n is in the range from 5 to 500 and in particular from 6 to 100;

polyamides corresponding to formula (VI) in which at least one of the groups Y and $Y^1$ contains at least one hydroxyl substituent;

polyamides of formula (III) synthesized with at least one portion of an activated diacid (diacid chloride, dianhydride or diester) instead of the diacid;

polyamides of formula (III) in which X represents —$(CH_2)_3$— or —$(CH_2)_{10}$; and polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:
- a $C_1$ to $C_{50}$ alkyl ester group by introducing a $C_1$ to $C_{50}$ monoalcohol during the synthesis,
- a $C_1$ to $C_{50}$ alkylamide group by taking as stopping group a monoacid if the silicone is $\alpha,\omega$-diaminated, or a monoamine if the silicone is an $\alpha,\omega$-dicarboxylic acid.

According to one embodiment variant of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based polyorganosiloxanes may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and better still 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a polyorganosiloxane based on a copolymer between a hydrocarbon-based polyamide and a silicone polyamide, by transamidation of a polyamide having, for example, an ethylene-diamine constituent, with an oligosiloxane-$\alpha,\omega$-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:
- by hydrosilylation of unsaturated bonds in polyamides based on fatty acid dimers;
- by silylation of the amide groups of a polyamide; or
- by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

According to another embodiment of the invention, the polyorganosiloxane consists of a homopolymer or a copolymer comprising urethane or urea groups.

As previously, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

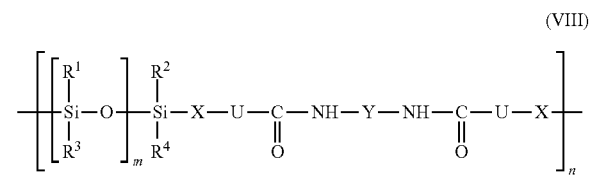

(VIII)

in which $R^1$, $R^2$, $R^3$, $R^4$, X, Y, m and n have the meanings given above for formula (I), and U represents —O— or —NH—, such that:

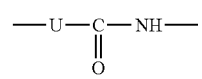

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4 and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

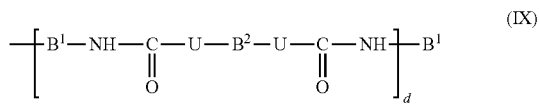

in which $B^1$ is a group chosen from the groups given above for Y, U is —O— or —NH— and $B^2$ is chosen from:

linear or branched $C_1$ to $C_{40}$ alkylene groups, which can optionally bear an ionizable group such as a carboxylic acid or sulphonic acid group, or a neutralizable or quaternizable tertiary amine group, $C_5$ to $C_{12}$ cycloalkylene groups, optionally bearing alkyl substituents, for example one to three methyl or ethyl groups, or alkylene, for example the diol radical: cyclohexanedimethanol, phenylene groups that may optionally bear $C_1$ to $C_3$ alkyl substituents, and groups of formula:

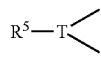

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

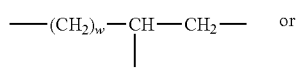

with w being an integer ranging from 1 to 10 and $R^5$ being a polyorganosiloxane chain.

When Y is a linear or branched $C_1$ to $C_{40}$ alkylene group, the —$(CH_2)_2$— and —$(CH_2)_6$— groups are preferred.

In the formula given above for Y, d may be an integer ranging from 0 to 5, preferably from 0 to 3 and more preferably equal to 1 or 2.

Preferably, $B^2$ is a linear or branched $C_1$ to $C_{40}$ alkylene group, in particular —$(CH_2)_2$— or —$(CH_2)_6$— or a group:

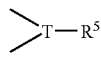

with $R^5$ being a polyorganosiloxane chain.

As previously discussed, the polyorganosiloxane may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

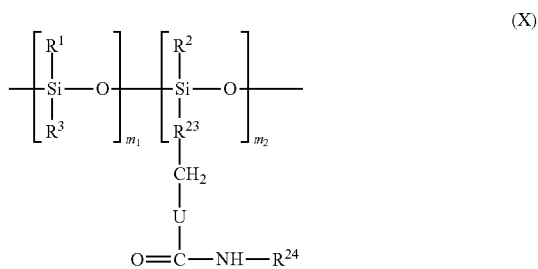

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used as gelling agents in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

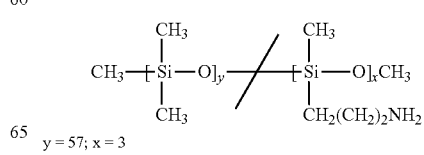

$y = 57; x = 3$

-continued

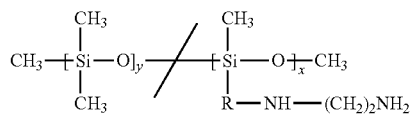

y = 56; x = 4

In these formulae, the symbol "/" indicates that the segments may be of different lengths and in a random order, and R represents a linear aliphatic group preferably containing 1 to 6 carbon atoms and better still 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polyorganosiloxanes that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

in which Ph is a phenyl group and n is a number from 0 to 300, in particular from 0 to 100, for example 50.

This polymer is obtained by reacting the following polysiloxane containing amino groups:

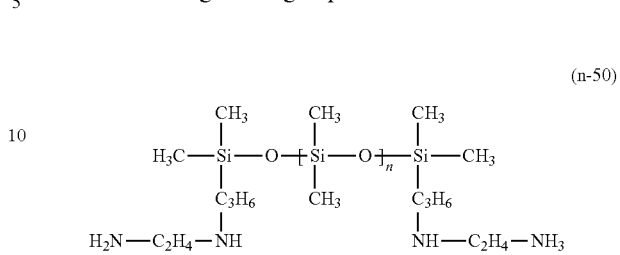

(n-50)

with phenyl isocyanate.

The polymers of formula (VIII) comprising urea or urethane groups in the chain of the silicone polymer may be obtained by reaction between a silicone containing $\alpha,\omega$-NH$_2$ or —OH end groups, of formula:

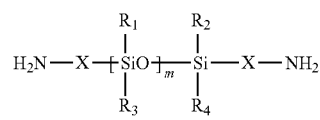

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^{2-}NH_2$ or HO—$B^{2-}$OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

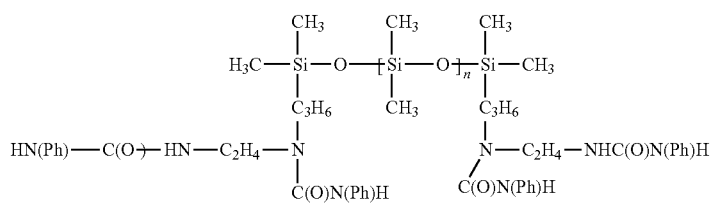

(XI)

(Ph = Phenyl)

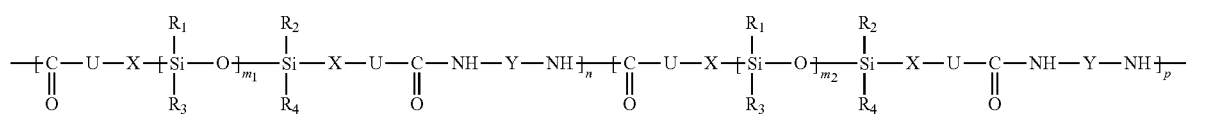

(XII)

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

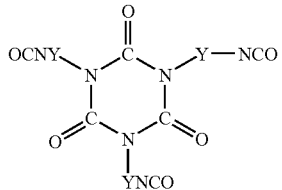

A polyurethane or polyurea silicone containing branches comprising an organosiloxane chain with groups capable of establishing hydrogen interactions is thus obtained. Such a polymer comprises, for example, a moiety corresponding to the formula:

with the portion corresponding to $m_1$ representing 1% to 99% by weight of the total weight of the polymer and the portion corresponding to $m_2$ representing 1% to 99% by weight of the total weight of the polymer;

mixtures of polymer of formula (VIII) combining 1) 80% to 99% by weight of a polymer in which n is equal to 2 to 10 and in particular 3 to 6, and 2) 1% to 20% of a polymer in which n is in the range from 5 to 500 and in particular from 6 to 100, copolymers comprising two moieties of formula (VIII) in which at least one of the groups Y contains at least one hydroxyl substituent;

polymers of formula (VIII) synthesized with at least one portion of an activated diacid (diacid chloride, dianhydride or diester) instead of the diacid;

polymers of formula (VIII) in which X represents —$(CH_2)_3$— or —$(CH_2)_{10}$—; and polymers of formula (VIII) in which the polymers end with a multifunctional chain chosen from the group consisting of monofunctional amines, monofunctional acids,

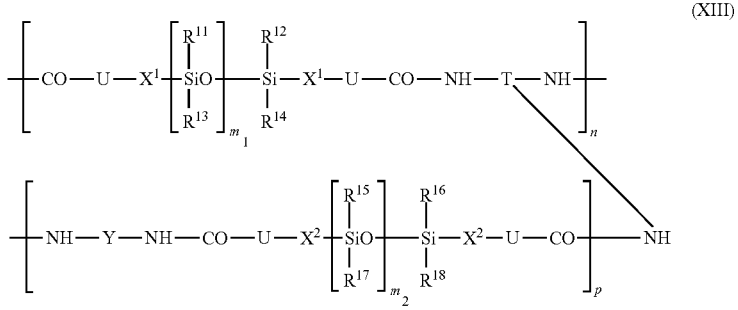

(XIII)

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1,000, and p is an integer ranging from 2 to 500.

As in the case of the polyamides, this copolymer can also comprise polyurethane silicone moieties without branching.

In another embodiment of the invention, the siloxane-based polyureas and polyurethanes that are preferred are:

polymers of formula (VIII) in which m is from 15 to 50;

mixtures of two or more polymers in which at least one polymer has a value of m in the range from 15 to 50 and at least one polymer has a value of m in the range from 30 to 50;

polymers of formula (XII) with $m_1$ chosen in the range from 15 to 50 and $m_2$ chosen in the range from 30 to 500 monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α,ω difunctional block of non-silicone nature, for example a polyester, a polyether or a polyolefin.

As has been seen previously, polyorganosiloxanes consisting of homopolymers or copolymers of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

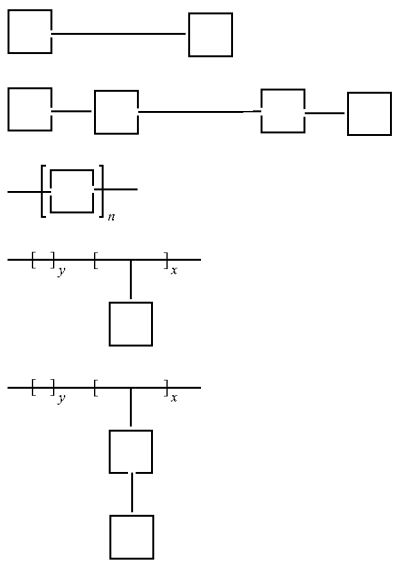

in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. The values n, x and y are such that the polymer has the desired properties in terms of an agent for gelling fatty phases based on silicone oil.

As examples of polymers that may be used, mention may be made of the silicone polyamides obtained in accordance with Examples 1 and 2 of document U.S. Pat. No. 5,981,680.

The polyorganosiloxanes advantageously have a softening point from 20 to 130° C. Preferably, they have a softening point ranging from 65 to 130° C. and better still from 70° C. to 130° C.

The at least one block copolymer may also be chosen from a polymer derived from (meth)acrylate copolymers such as those disclosed in U.S. Pat. No. 6,066,313, the entire content of which is hereby incorporated by reference. These (meth) acrylate copolymers may be random, block or grafted.

A variety of (meth)acrylate ester monomer repeat units may be used to make the polymer, including aliphatic esters of (meth)acrylic acid like those obtained with the esterification of (meth)acrylic acid with an aliphatic alcohol of 2 to 30, preferably 2 to 20, more preferably 2 to 8 carbon atoms. If desired, the aliphatic alcohol may have one or more hydroxy groups.

Preferably, the polymer is made from ethylenically unsaturated monomer repeat units having the following general formula:

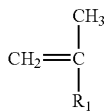

wherein $R_1$ is COOM wherein M is a substituted or unsubstituted $C_{1-30}$ straight or branched chain alkyl where the substituents are halogen or alkoxy.

Preferably, $R_1$ is COOM where M is a $C_{1-5}$ alkyl, and most preferably a branched chain $C_{1-5}$ alkyl such as isobutyl.

Preferably the polymer derived from (meth)acrylate copolymers has a glass transition temperature of from −50 to 110° C., preferably from 0 to 70° C., more preferably 20 to 65° C., and contains at least one repeat unit which, if polymerized to a molecular weight average of about 20,000, has a glass transition temperature of about −50 to 110° C., preferably from 0 to 70° C., more preferably 20 to 65° C.; and has a molecular weight of about 5,000 to 300,000, preferably 5,000 to 50,000.

Preferably the polymer derived from (meth)acrylate copolymers is soluble in solvents such as paraffinic hydrocarbons, particularly isododecane. Most preferably, the polymer is in the form of a solution comprising 1-90% by weight polymer and 10-99% by weight solvent, where the solvent is preferably a paraffinic hydrocarbon, most preferably isododecane.

Examples of suitable monomer units which may be used to make the polymers derived from (meth)acrylate copolymers include, but are not limited to, those set forth below:
Repeat Unit
isobutyl(meth)acrylate
pentyl(meth)acrylate
2-methoxyethyl(meth)acrylate
propyl(meth)acrylate
hexyl(meth)acrylate
fluoro(meth)acrylate
2-ethylhexyl(meth)acrylate
Hexadecyl(meth)acrylate
Isonorbornyl(meth)acrylate
Cyclohexyl(meth)acrylate
Polyalkylene oxide(meth)acrylate
Aliphatic urethane(meth)acrylate The polymers derived from (meth)acrylate copolymers can be prepared by conventional free radical polymerization techniques in which the monomer, solvent, and polymerization initiator are charged over a 1-24 hour period of time, preferably 2-8 hours, into a conventional polymerization reactor in which the constituents may be heated to about 60-175° C., preferably 80-100° C. The polymers derived from (meth)acrylate copolymers may also be made by emulsion polymerization or suspension polymerization using conventional techniques. Also, anionic polymerization or Group Transfer Polymerization (GTP) is another method by which the copolymers used in the invention may be made. GTP is well known in the art and disclosed in U.S. Pat. Nos. 4,414,372; 4,417,034; 4,508,880; 4,524,196; 4,581,428; 4,588,795; 4,598,161; 4,605,716; 4,605,716; 4,622,372; 4,656,233; 4,711,942; 4,681,918; and 4,822,859; all of which are hereby incorporated by reference. Preferably, the polymers used in the compositions of the invention are made by GTP procedures set forth in U.S. Pat. Nos. 4,588,795 and 4,605,716.

The at least one block copolymer may also include those derived from silicone/(meth)acrylate copolymers, such as those as described in U.S. Pat. Nos. 5,061,481, 5,219,560, and 5,262,087, the disclosures of which are hereby incorporated by reference. Also included are those derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the product sold under the tradename KP-545, or acrylates/stearyl acrylate/dimethicone acrylates copolymers, such as those commercially available from Shin-Etsu, for example, the product sold under the tradename KP-561, and acrylates/behenyl acrylate/dimethicone acrylates copolymer, such as those commercially available from Shin-Etsu, for example, the product sold under the tradename KP-562.

Further non-limiting examples include polymers comprising a backbone chosen from vinyl polymers, methacrylic polymers, and acrylic polymers and at least one chain chosen from pendant siloxane groups and pendant fluorochemical groups. Non-limiting examples of such polymers comprise at least one unit derived from at least one A monomer, at least one unit derived from at least one C monomer, at least one unit derived from D monomers, and, optionally, at least one unit derived from at least one B monomer, wherein:

A, which may be identical or different, are each chosen from free-radically-polymerizable acrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols, and free-radically-polymerizable methacrylic esters of at least one alcohol chosen from 1,1,-dihydroperfluoroalkanols, omega-hydridofluoroalkanols, fluoroalkylsulfonamido alcohols, cyclic fluoroalkyl alcohols, and fluoroether alcohols, and analogs of any of the foregoing at least one alcohols;

B, which may be identical or different, are each chosen from reinforcing monomers which are copolymerizable with at least one A monomer;

C, which may be identical or different, are each chosen from monomers having the formula:

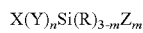

wherein

X is chosen from vinyl groups which are copolymerizable with at least one A monomer and at least one B monomer, Y is chosen from divalent allylene groups, divalent arylene groups, divalent alkarylene groups, and divalent aralkylene groups, wherein the groups comprise from 1 to 30 carbon atoms, and further wherein the groups optionally further comprise at least one group chosen from ester groups, amide groups, urethane groups, and urea groups;

n is zero or 1;

m is a number ranging from 1 to 3;

R, which may be identical or different, are each chosen from hydrogen, $C_1$-$C_4$ alkyl groups, aryl groups, and alkoxy groups; and Z, which may be identical or different, are each chosen from monovalent siloxane polymeric groups; and D, which may be identical or different, are each chosen from free-radically-polymerizable acrylate copolymers and free-radically-polymerizable methacrylate copolymers. Such polymers and their manufacture are disclosed in U.S. Pat. Nos. 5,209,924 and 4,972,037, and WO 01/32737, the disclosures of which are hereby incorporated by reference.

Further non-limiting examples include polymers comprising at least one A monomer, at least one C monomer, and at least one D monomer, wherein A, which may be identical or different, are each chosen from polymerizable acrylic esters of at least one fluoroalkylsulfonamido alcohol and polymerizable methacrylic esters of at least one fluoroalkylsulfonamido alcohol, D, which may be identical or different, are each chosen from methacrylic acid esters of at least one $C_1$-$C_{12}$ linear alcohol and methacrylic acid esters of at least one $C_1$-$C_2$ branched alcohol, and C is as defined above. Such polymers include polymers comprising at least one group of the formula:

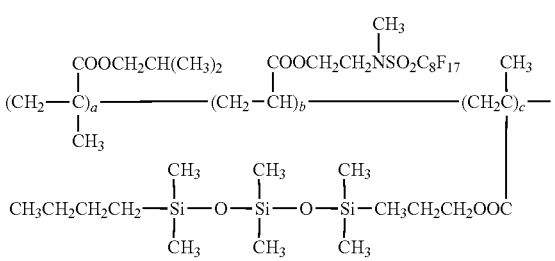

wherein a, b, and c, which may be identical or different, are each a number ranging from 1 to 100,000; and the terminal groups, which may be identical or different, are each chosen from $C_1$-$C_{20}$ linear alkyl groups, $C_3$-$C_{20}$ branched chain alkyl groups, $C_3$-$C_{20}$ aryl groups, $C_1$-$C_{20}$ linear alkoxy groups, and $C_3$-$C_{20}$ branched alkoxy groups.

Such polymers are disclosed in U.S. Pat. Nos. 4,972,037, 5,061,481, 5,209,924, 5,849,275, and 6,033,650, and WO 93/23446 and WO 95/06078, the disclosures of which are hereby incorporated by reference. These polymers may be purchased from Minnesota Mining and Manufacturing Company under the tradenames "Silicone Plus" polymers. For example, poly(isobutyl methacrylate-co-methyl FOSEA)-g-poly(dimethylsiloxane) is sold under the tradename SA 70-5 IBMMF.

Other non-limiting examples include silicone/acrylate graft terpolymers, for example, those having the formula:

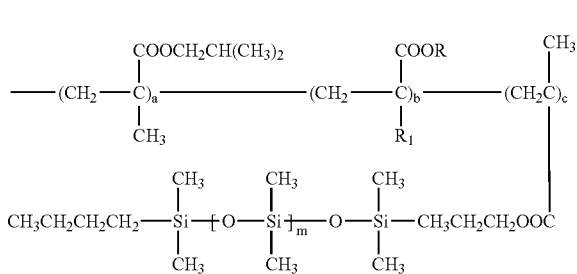

wherein a, b, and c are present in a weight ratio of 69.9:0.1:30 respectively,

R and $R^1$, which may be identical or different, are each chosen from hydrogen and $C_1$-$C_6$ alkyl groups; and m is a number ranging from 100-150.

According to preferred embodiments, m is chosen to provide a macromer having a molecular weight ranging from 8,000 to 12,000, such as 10,000. In another embodiment, m is a number ranging from 124-135, such as 130. Non-limiting examples of these copolymers are described in WO 01/32727 A1, the disclosure of which is hereby incorporated by reference.

According to other preferred embodiments, the polymer comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903, 4,981,902, the disclosures of which are hereby incorporated by reference.

In preferred embodiments the polymer comprises at least one A monomer, at least one C monomer, and, optionally at least one B monomer, wherein the at least one A monomer is chosen from free-radically-polymerizable vinyl monomers, free-radically-polymerizable methacrylate monomers, and free-radically-polymerizable acrylate monomers; the at least one B monomer, if present, is chosen from at least one reinforcing monomer copolymerizable with the at least one A monomer, and the at least one C monomer is chosen from monomers having the formula:

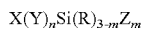

wherein:

X is chosen from vinyl groups which are copolymerizable with the at least one A monomer and with the at least one B monomer;

Y is chosen from divalent groups;

n is zero or 1;

m is a number ranging from 1 to 3;

R, which may be identical or different, are each chosen from hydrogen, optionally substituted $C_1$-$C_{10}$ alkyl groups, optionally substituted phenyl groups, and optionally substituted $C_1$-$C_{10}$ alkoxy groups; and Z, which may be identical or different, are each chosen from monovalent siloxane polymeric groups.

Non-limiting examples of A monomers include methacrylic acid esters of $C_1$-$C_{12}$ linear alcohols, methacrylic acid esters of $C_1$-$C_{12}$ of branched alcohols, styrene monomers, vinyl esters, vinyl chloride monomers, vinylidene chloride monomers, and acryloyl monomers.

Non-limiting examples of B monomers include acrylic monomers comprising at least one group chosen from hydroxyl, amino, and ionic groups, and methacrylic monomers comprising at least one group chosen from hydroxyl, amino, and ionic groups. Non-limiting examples of ionic groups include quaternary ammonium groups, carboxylate salts, and sulfonic acid salts.

The C monomers are as defined above.

In yet another preferred embodiment, the polymer is chosen from vinyl-silicone graft copolymers having the following formula and vinyl-silicone block copolymers having the following formula:

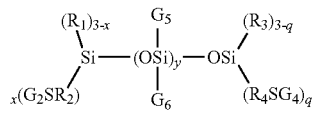

wherein $G_5$, which may be identical or different, are each chosen from alkyl groups, aryl groups, aralkyl groups, alkoxy groups, alkylamino groups, fluoroalkyl groups, hydrogen, and-ZSA groups, wherein, A is chosen from vinyl polymeric segments comprising at least one polymerized free-radically-polymerizable monomer, and Z is chosen from divalent $C_1$-$C_{10}$ alkylene groups, divalent aralkylene groups, divalent arylene groups, and divalent alkoxylalkylene groups. In a preferred embodiment Z is chosen from methylene groups and propylene groups.

$G_6$, which may be identical or different, are each chosen from alkyl groups, aryl groups, aralkyl groups, alkoxy groups, alkylamino groups, fluoroalkyl groups, hydrogen, and-ZSA groups, as defined above;

$G_2$ comprises A;

$G_4$ comprises A.

$R_1$, which may be identical or different, are each chosen from alkyl groups, aryl groups, aralkyl groups, alkoxy groups, alkylamino groups, fluoroalkyl groups, hydrogen, and hydroxyl. In one embodiment, $R_1$ is chosen from $C_1$-$C_4$ alkyl groups, such as methyl groups, and hydroxyl.

$R_2$, which may be identical or different, are each chosen from divalent $C_1$-$C_{10}$ alkylene groups, divalent arylene groups, divalent aralkylene groups, and divalent alkoxyalkylene groups. In one embodiment, $R_2$ is chosen from divalent $C_1$-$C_3$ alkylene groups and divalent $C_7$-$C_{10}$ aralkylene groups. In another embodiment, $R_2$ is chosen from —$CH_2$— groups and divalent 1,3-propylene groups.

$R_3$, which may be identical or different, are each chosen from alkyl groups, aryl groups, aralkyl groups alkoxy groups, alkylamino groups, fluoroalkyl groups, hydrogen, and hydroxyl. In one embodiment, $R_3$ is chosen from $C_1$-$C_4$ alkyl groups and hydroxyl. In another embodiment, $R_3$ is chosen from methyl groups.

$R_4$, which may be identical or different, are each chosen from divalent $C_1$-$C_{10}$ alkylene groups, divalent arylene groups, divalent aralkylene groups, and divalent alkoxyalkylene groups. In one embodiment, $R_4$ is chosen from divalent $C_1$-$C_3$ alkylene groups and divalent $C_7$-$C_{10}$ aralkylene groups. In another embodiment, $R_4$ is chosen from divalent —$CH_2$— groups and divalent 1,3-propylene groups.

x is a number ranging from 0 to 3;

y is a number greater than or equal to 5. In an embodiment, y ranges from 10 to 270, and in another embodiment, y ranges from 40 to 270.

q is a number ranging from 0 to 3;

Non-limiting examples of these polymers are described in U.S. Pat. No. 5,468,477, the entire contents of which is hereby incorporated by reference. A non-limiting example of such polymers is poly(dimethylsiloxane)-g-poly(isobutyl methacrylate), which is commercially available from 3M Company under the tradename VS 70 IBM.

Other block copolymers which may also be mentioned are chosen, for example, from liposoluble homopolymers, such as those resulting from the homopolymerization of a vinyl ester containing from 9 to 22 carbon atoms, alkyl acrylates and alkyl methacrylates, wherein the alkyl groups contain from 10 to 20 carbon atoms.

Such block copolymers may be chosen, for example, from polyvinyl stearate, polystearyl(meth)acrylate, polyvinyl laurate, and polylauryl(meth)acrylate.

The block copolymers defined above are known and are disclosed, for example, in patent application FR 2,232,303 A which is hereby incorporated by reference. They may have a weight-average molecular weight ranging from 2,000 to 500,000, such as, for example, from 4,000 to 200,000.

The block copolymer is generally present in the cosmetic composition in an amount ranging from greater than 0% to 95% by weight; greater than 0% to 75% by weight; greater than 0% to 50% by weight; greater than 0% to 25% by weight; greater than 0% to 15% by weight, based on the weight of the composition.

Tackifier

A substance is described as a tackifier if, by adding it to a block copolymer, the resulting composition has the properties of a pressure sensitive adhesive. In general, tackifiers can be divided into four different families in terms of their chemistry: hydrocarbon resins, terpenes, amorphous (i.e. non-crystalline) rosins, rosin esters and their derivatives, and pure monomer resins. These tackifiers are characterized by their compatibility with at least one segment of the block copolymer. By the term "compatible", it is meant that when the block copolymer and tackifier are mixed, the combination of at least one segment of the block copolymer with the tackifier forms a polymer blend having a single glass transition temperature $T_g$ which may be measured by DMA, DSC or neutron light scattering.

The compatibility of the block copolymer and the tackifier may also be defined in terms of solubility parameters. The solubility parameter δ according to the Hansen solubility space is defined in the article "*Solubility Parameter Values*" by Eric A. Grulke in the work "*Polymer Handbook*" 3rd edition, Chapter VII, pages 519-559, the entire content of which is hereby incorporated by reference, by the relationship:

$\delta=(d_D^2+d_P^2+d_H^2)^{1/2}$, in which:

$d_D$ characterizes the London dispersion forces resulting from the formation of dipoles induced during molecular impacts, $d_P$ characterizes the forces of Debye interactions between permanent dipoles, $d_H$ characterizes the forces of specific interactions (hydrogen bond, acid/base or donor/acceptor type and the like). The definition of the solvents in the three-dimensional solubility space according to Hansen is given in the article by C. M. Hansen: "*The three-dimensional solubility parameters*" J. Paint Technol., 39, 105(1967), the entire content of which is hereby incorporated by reference.

The at least one tackifier used in the present invention will have a solubility parameter corresponding to δ and the block copolymer will have at least one segment whose solubility parameter corresponds to δ±2, preferably δ±1.7, more preferably δ±1.5, more preferably δ±1.3, more preferably δ±1.0, more preferably δ±0.7, more preferably δ±0.5, and more preferably δ±0.3.

Examples of suitable tackifiers, include, but are not limited to, aliphatic hydrocarbon resins, aromatic modified aliphatic hydrocarbon resins, hydrogenated polycyclopentadiene resins, polycyclopentadiene resins, gum rosins, gum rosin esters, wood rosins, wood rosin esters, tall oil rosins, tall oil rosin esters, polyterpenes, aromatic modified polyterpenes, terpene phenolics, aromatic modified hydrogenated polycyclopentadiene resins, hydrogenated aliphatic resin, hydrogenated aliphatic aromatic resins, hydrogenated terpenes and modified terpenes, hydrogenated rosin acids, hydrogenated rosin esters, polyisoprene, partially or fully hydrogenated polyisoprene, polybutenediene, partially or fully hydrogenated polybutenediene, and the like. As is evidenced by some of the cited examples, the tackifier may be fully or partially hydrogenated. The tackifier may also be non-polar. (Non-polar meaning that the tackifier is substantially free of monomers having polar groups. Preferably, the polar groups are not present, however, if they are present, they are preferably present in an amount of up to about 5% by weight, preferably up to about 2% by weight, and more preferably up to about 0.5% by weight.) In some embodiments, the tackifier may have a softening point (Ring and Ball, as measured by ASTM E-28) of 80° C. to 150° C., preferably 100° C. to 130° C. In other embodiments the tackifier may be liquid and have an R and B softening point of between about −70 and 70° C.

In some embodiments, the tackifiers are hydrogenated hydrocarbon resins such as a hydrogenated styrene/methyl styrene/indene copolymer e.g., styrene/methyl styrene/indene copolymers which include R1090, R1100, R7100, S1100, and S5100, all which are commercially available from Eastman Chemical under the trade name Regalite®. In other embodiments, aliphatic or aromatic hydrocarbon-based tackifying resins, for instance the resins sold under the name "Piccotac" and "Hercotac" from Hercules or "Escorez" from Exxon, may also be used. It is also to be understood that mixtures of tackifiers may also be employed without departing from the spirit of the invention.

The tackifier is present in the cosmetic composition of the present invention in an amount ranging from greater than 0% to 90% by weight; greater than 0% to 60% by weight; greater than 0% to 40% by weight; greater than 0% to 20% by weight; greater than 0% to 10% by weight, based on the weight of the composition.

Phenylated Silicones

The composition according to the invention also contains at least one phenylated silicone. Examples of suitable phenylated silicones include, but are not limited to, polyphenylmethylsiloxanes, and phenyltrimethicones.

The phenylated silicones useful in the present invention preferably have an average number molecular weight of: up to 200,000; up to 150,000; up to 100,000; up to 50,000; up to 20,000; up to 10,000.

Suitable phenylated silicones include, but are not limited to, those commercialized under the trade name "Abil AV 8853" by Goldschmidt, those commercialized under the trade names "DC 556" and "SF 558" by Dow Corning, and those commercialized under the trade name "Silbione 70633 V 30" by Rhone-Poulenc.

Additional examples of suitable phenylated silicones include, but are not limited to, those commercialized by Wacker Silicones such as Belsil PDM 20, a phenylated silicone with a viscosity at 25° C. of approximately 20 cSt; Belsil PDM 200, a phenylated silicone with a viscosity at 25° C. of approximately 200 cSt; Belsil PDM 1000, a phenylated silicone with a viscosity at 25° C. of approximately 1000 cSt.

The phenylated silicone will typically be present in the composition of the invention in an amount ranging from greater than 0% to 90% by weight; greater than 0% to 50% by weight; greater than 0% to 30% by weight; greater than 0% to 20% by weight; greater than 0% to 10% by weight, based on the total weight of the composition.

Solvent

The cosmetic compositions of the present invention also contain at least one solvent selected from volatile solvents and nonvolatile solvents. The expression "volatile solvent" means a solvent that is capable of evaporating at room temperature from a support onto which it has been applied, in other words a solvent which has a measurable vapor pressure at room temperature. See, U.S. Pat. No. 6,656,458, the entire content of which is hereby incorporated by reference. Representative examples of volatile organic solvents include volatile hydrocarbon-based oils. The expression "hydrocarbon-based oil" means an oil containing only hydrogen and carbon atoms. Examples of volatile hydrocarbon-based oils include isoparaffins, i.e., branched alkanes containing from 8 to 16 carbon atoms, and in particular isododecane (also known as 2,2,4,4,6-pentamethylheptane). It is also possible to use mixtures of such isoparaffins. Other volatile hydrocarbon-based oils, such as petroleum distillates, can also be used. See, U.S. Pat. No. 6,406,502, the entire content of which is hereby incorporated by reference. Yet other examples of organic solvents include volatile silicones such as, for example, cyclic volatile silicone oils, such as cyclomethicone, octamethylcyclotetrasiloxane, decamethylcyclopentasiloxane, dodecamethylcyclohexasiloxane, linear volatile silicones such as octamethyltrisiloxane, heptamethylhexyltrisiloxane and heptamethyloctyltrisiloxane, or alternatively volatile fluoro oils such as nonafluoromethoxybutane or perfluoromethylcyclopentane.

Nonvolatile solvents which can be used in the invention include, but are not limited to, monoesters, diesters, triesters, mixed aliphatic and/or aromatic, polar oils such as: hydrocarbon-based oils of animal origin, such as perhydrosqualene; hydrocarbon-based plant oils such as liquid triglycerides of fatty acids and of glycerol, in which the fatty acids may have varied chain lengths, these chains being linear or branched, and saturated or unsaturated; these oils can be chosen, for example, from wheat germ oil, sunflower oil, corn oil, soybean oil, marrow oil, grapeseed oil, blackcurrant seed oil, sesame oil, hazelnut oil, apricot oil, macadamia oil, castor oil, avocado oil, karite butter, sweet almond oil, cotton oil, alfalfa oil, poppy oil, pumpkin oil, evening primrose oil, millet oil, barley oil, quinoa oil, olive oil, rye oil, safflower oil, candlenut oil, passion flower oil, musk rose oil, and caprylic/capric acid triglycerides such as those sold by the company Stearineries Dubois or those sold under the names Miglyol 810, 812 and 818 by the company Dynamit Nobel; natural or synthetic esters of formula $R_1COOR_2$, wherein $R_1$ is a higher fatty acid residue comprising 7 to 19 carbon atoms, and $R_2$ is a linear or branched hydrocarbon-based chain comprising 3 to 20 carbon atoms, such as, for example, purcellin oil (cetostearyl octanoate), isopropyl myristate, isopropyl palmitate and isostearyl palmitate, and alkyl or polyalkyl octanoates, decanoates or ricinoleates; synthetic ethers of formula $R^3COR^4$, wherein $R^3$ is a $C_3$ to $C_{19}$ alkyl radical, and $R^4$ is a $C_3$ to $C_{20}$ alkyl radical; fatty alcohols comprising at least 12 carbon atoms, such as octyldodecanol or oleyl alcohol; cyclic hydrocarbons such as (alkyl)cycloalkanes, wherein the alkyl chain is linear or branched, saturated or unsaturated and comprises 1 to 30 carbon atoms, such as cyclohexane or dioctylcyclohexane; aromatic hydrocarbons, for example, alkenes such as benzene, toluene, 2,4-dimethyl-3-cyclohexene, dipentene, p-cymene, naphthalene or anthracene, and esters such as isostearyl benzoate or alkyl benzoate; primary, secondary or tertiary amines such as triethanolamine; and mixtures thereof. In one embodiment, synthetic esters such as isopropyl myristate, isopropyl palmitate and/or isostearyl palmitate are used.

It may also be desirable to add one or more nonvolatile apolar solvents to the above polar nonvolatile solvents. Examples of suitable apolar solvents include, but are not limited to: silicone oils such as polydimethylsiloxanes that are liquid at room temperature, phenyldimethicones, phenyltrimethicones, polymethylphenylsiloxanes, alkylpolydimethylsiloxanes comprising a $C_2$ to $C_{20}$ alkyl chain, and mixtures thereof; and linear or branched hydrocarbons of synthetic or mineral origin, for example, nonvolatile liquid paraffins and derivatives thereof, petroleum jelly, polydecenes, hydrogenated polyisobutene such as parleam, and mixtures thereof. These apolar oils can be used as the sole nonvolatile solvent or in a mixture of nonvolatile solvents.

In the event that the composition is a cosmetic composition containing, as the at least one block copolymer, a thermoplastic elastomer having a styrene content of greater than 30% by weight, based on the weight of the elastomer, then a solvent and/or functional ingredient capable of dissolving a styrene block must also be present in the composition in order to enhance its ease of application onto keratinous surfaces. One example thereof is a solvent containing at least one aromatic group such as an alkyl benzoate or benzyl alcohol or phenoxyethanol. The specific solvent and/or functional ingredient, including the amount to be used, will depend on the type of cosmetic product being formulated and will thus be apparent to those skilled in the art of cosmetic formulation.

The solvent is typically present in the composition of the invention in an amount of from greater than 0% to 95% by weight; greater than 0% to 75% by weight; greater than 0% to 50% by weight; greater than 0% to 25% by weight; greater than 0% to 10% by weight, based on the weight of the composition.

Colorant

The cosmetic compositions of the present invention may also contain at least one cosmetically acceptable colorant such as a pigment or dyestuff. Examples of suitable pigments include, but are not limited to, inorganic pigments, organic pigments, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on Cochineal Carmine (CI 75,570) and mixtures thereof. A preferred organic pigment is carbon black.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof.

The precise amount and type of colorant employed in the compositions of the present invention will depend on the color, intensity and use of the cosmetic composition and, as a result, will be determined by those skilled in the art of cosmetic formulation.

In some embodiments, it may be desirable to formulate cosmetic compositions in accordance with the present invention which are free of wax. However, in the event that a wax is employed, it will be present in an amount of from about 0.1% to about 60% by weight, based on the total weight of the composition. Suitable waxes are those generally used in cosmetics and dermatology. Examples thereof include, but are not limited to, those of natural origin such as beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil. Examples of suitable synthetic waxes include, but are not limited to, polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly(di)methylsiloxanes and/or poly(di)methyl-siloxane esters that are solid at 40° C., for example, at above 55° C.

The compositions of the present invention may further comprise at least one cosmetically or dermatologically acceptable additive such as a thickener, a plasticizer, a film former, an antioxidant, an essential oil, a preserving agent, a fragrance, a filler, a pasty fatty substance, a waxy fatty substance, a neutralizing agent, and a polymer, and cosmetically active agents and/or dermatological active agents such as, for example, emollients, moisturizers, vitamins, essential fatty acids and medicaments.

The compositions of the invention may also be optionally thickened with an oil-phase thickener or at least one agent useful for gelling a liquid fatty phase. The thickening agent increases the liquid fatty phase viscosity and leads to a solid or flowable composition when introduced in said fatty phase. The thickening agent does not encompass waxes, in the sense that it is not waxy. The at least one gelling agent may be chosen from gelling agents in polymeric form and gelling agents in mineral form. The gelling agent is preferably selected from the group consisting of agents that gel via chemical reticulation and agents that gel via physical reticulation.

Modified clays may be used as gelling agents, examples of which include, but are not limited to, hectorites modified with an ammonium chloride of a $C_{10}$ to $C_{22}$ fatty acid, such as hectorite modified with distearyldimethylammonium chloride, also known as quaternium-18 bentonite, such as the products sold or made under the names Bentone 34 by the company Rheox, Claytone XL, Claytone 34 and Claytone 40 sold or made by the company Southern Clay, the modified clays known under the name quaternium-18 benzalkonium bentonites and sold or made under the names Claytone HT, Claytone GR and Claytone PS by the company Southern Clay, the clays modified with stearyldimethylbenzoylammonium chloride, known as stearalkonium bentonites, such as the products sold or made under the names Claytone APA and Claytone AF by the company Southern Clay, and Baragel 24 sold or made by the company Rheox.

As other mineral gelling agents, which can be used in the invention, mention may be made of silica, such as fumed silica. The fumed silica may have a particle size, which may be nanometric to micrometric, for example ranging from about 5 nm to 200 nm.

The fumed silicas may be obtained by high-temperature hydrolysis of a volatile silicon compound in a hydrogen-oxygen flame, producing a finely divided silica. This process makes it possible to obtain hydrophilic silicas that have a large number of silanol groups at their surface. Such hydrophilic silicas are sold or made, for example, under the names "Aerosil 130®", "Aerosil 200®", "Aerosil 255®", "Aerosil 300®" and "Aerosil 380®" by the company Degussa, and "CAB-O-SIL HS-5®", "CAB-O-SIL EH-5®", "CAB-O-SIL LM-130®", "CAB-O-SIL MS-55®" and "CAB-O-SIL M-5®" by the company Cabot.

It is thus possible to chemically modify the surface of the hydrophilic silica by chemical reaction, producing a reduction in the number of silanol groups. The silanol groups can be replaced, for example, with hydrophobic groups: this then gives a hydrophobic silica. The hydrophobic groups may be: trimethylsiloxyl groups, which are obtained in particular by treating fumed silica in the presence of hexamethyldisilazane. Silicas thus treated are known as "silica silylate" according to the CTFA (6th edition, 1995). They are sold or made, for example, under the references "Aerosil R812®" by the company Degussa and "CAB-O-SIL TS-530®" by the company Cabot; dimethylsilyloxyl or polydimethylsiloxane groups, which are obtained in particular by treating fumed silica in the presence of polydimethylsiloxane or dimethyldichlorosilane. Silicas thus treated are known as "silica dimethyl silylate" according to the CTFA (6th edition, 1995). They are sold or made, for example, under the references "Aerosil R972®" and "Aerosil R974®" by the company Degussa, and "CAB-O-SIL TS-610®" and "CAB-O-SIL TS-720®" by the company Cabot; groups derived from reacting fumed silica with silane alkoxides or siloxanes. These treated silicas are, for example, the products sold or made under the reference "Aerosil R805®"by the company Degussa.

According to the invention, hydrophobic silica, such as fumed silica, may be used as lipophilic gelling agent. The use of fumed silica makes it possible to obtain a translucent or even transparent composition, in particular in the form of a stick, which does not exude, in the absence of opacifying particles such as waxes, fillers and pigments (including nacres).

The at least one liposoluble gelling agent can allow the exudation of the composition to be limited and can allow its stability to be increased, while at the same time conserving the composition's glossy appearance, which is not possible with waxes such as those used conventionally in cosmetics and dermatology.

Water-soluble thickeners or gelling agents that may be used include, but are not limited to, crosslinked acrylates (e.g. Carbopol 982), hydrophobically-modified acrylates (e.g. Carbopol 1382); polyacrylamides such as, for example, the crosslinked copolymers sold under the names Sepigel 305 (CTFA name: polyacrylamide/C13-C14 isoparaffin/Laureth 7) or Simulgel 600 (CTFA name: acrylamide/sodium acryloyldimethyltaurate copolymer/isohexadecane/polysorbate 80) by SEPPIC; 2-acrylamido-2-methylpropanesulphonic acid polymers and copolymers, that are optionally crosslinked and/or neutralized; cellulose derivatives such as hydroxyethylcellulose, sodium carboxymethylcellulose, hydroxypropyl methylcellulose, hydroxypropyl cellulose, ethyl cellulose and hydroxymethyl cellulose; polysaccharides and gums, e.g., natural gums such as xanthan gum, sclerotium, carrageenan and pectin; and mixtures thereof.

Other examples of water-soluble thickeners include xanthan gum, carob gum, scleroglucan gum, gellan gum, rhamsan gum and karaya gum, alginates, maltodextrin, polysaccharide resins such as starch and its derivatives, hyaluronic acid and its salts, clays, and, in particular, montmorillonites, hectorites, bentonites, and laponites, crosslinked polyacrylic acids, such as the "Carbopol" products from the company Goodrich, the polyglyceryl (meth)acrylate polymers sold under the names "Hispagel" or "Lubragel" by the companies Hispano Quimica or Guardian, polyvinylpyrrolidone (PVP), polyvinyl alcohol, crosslinked acrylamide polymers and copolymers, such as those sold under the names "PAS 5161" or "Bozepol C" by the company Hoechst, "Sepigel 305" by the company SEPPIC, cross linked methacryloyloxyethyltrimethylammonium chloride homopolymers sold under the name "Salcare SC95" by the company Allied Colloid, and associative polymers and, in particular, associative polyurethanes.

The at least one thickening/gelling agent, if used, will typically be present in an amount of from about 0.1% to about 20% by weight, preferably from about 0.5% to about 15% by weight, and more preferably from about 1 to about 10% by weight, based on the weight of the composition.

While the use of a plasticizer is not necessary in the cosmetic compositions of the present invention, its use may, at times, be desirable. Plasticizers are organic compounds added to a high polymer both to facilitate processing and to increase the flexibility and toughness of the final product by internal modification of the polymer molecule. Examples of plasticizers include, but are not limited to, oils, cellulose esters, phthalate esters, adipate esters, sebacate esters, ethylene glycol, tricresyl phosphate, and castor oil. Representative examples of plasticizers which may be included are glycol ethers, benzyl alcohol, triethyl citrate, 1,3-butylene glycol and propylene carbonate. A plasticizer, if used, will typically be present in an amount of from about 1 to about 70% by weight, preferably from about 2 to about 50% by weight, and more preferably from about 5 to about 30% by weight, based on the weight of the composition.

The composition according to the invention may also comprise additional polymers such as conventional film-forming polymers. Examples of suitable additional polymers include, but are not limited to: keratin derivatives, such as keratin hydrolysates and sulphonic keratins; anionic, cationic, amphoteric or nonionic derivatives of chitin or chitosan; cellulose derivatives such as hydroxyethylcellulose, hydroxypropylcellulose, methylcellulose, ethylhydroxyethylcellulose, carboxymethylcellulose, and quaternized derivatives of cellulose; acrylic polymers or copolymers, such as polyacrylates or polymethacrylates; polyvinylpyrrolidones (PVP) and vinyl copolymers, such as methyl vinyl ether-maleic anhydride copolymers, or vinyl acetate-crotonic acid copolymer; water-dispersible anionic polyesteramide and/or polyester polymers comprising monomers bearing a functional group —$SO_3M$, in which M represents a hydrogen atom, an ammonium ion $NH_4^+$ or a metal ion, such as, for example, an $Na^+$, $Li^+$, $K^+$, $Mg^{2+}$, $Ca^{2+}$, $Cu^{2+}$, $Fe^{2+}$ or $Fe^{3+}$ ion; polyurethane polymers, especially anionic, cationic, nonionic or amphoteric polyurethanes, acrylic polyurethanes, polyvinylpyrrolidone polyurethanes, polyester polyurethanes, polyether polyurethanes, polyureas, polyurea/polyurethanes, and mixtures thereof; and polymers of natural origin, modified if desired, such as gum arabic, guar gum, xanthan derivatives, karaya gum; alginates and carragheenates; glycoaminoglycans, hyaluronic acid and its derivatives; shellac, sandarac gum, dammars, elemis and copals, are also useful.

The additional polymer, if used, will be present in an amount of from about 0.01 to about 20% by weight, preferably from about 0.1 to about 15% by weight, and most preferably from about 0.5 to about 10% by weight, based on the weight of the composition.

Representative examples of preservatives include alkyl para-hydroxybenzoates, wherein the alkyl radical has from 1, 2, 3, 4, 5 or 6 carbon atoms and preferably from 1 to 4 carbon atoms e.g., methyl para-hydroxybenzoate (methylparaben), ethyl para-hydroxybenzoate (ethylparaben), propyl para-hydroxybenzoate (propylparaben), butyl para-hydroxybenzoate (butylparaben) and isobutyl para-hydroxybenzoate (isobutylparaben). Mixtures of preservatives may certainly be used, e.g., the mixture of methyl-paraben, ethylparaben, propylparaben and butylparaben sold under the name Nipastat by Nipa, and the mixture of phenoxyethanol, methylparaben, ethylparaben, propylparaben and butylparaben sold under the name Phenonip, also by Nipa. These preservatives may be present in amounts ranging from about 0.01 to about 10% by weight, preferably from 0.5% to about 5% by weight, and more preferably from about 0.8 to about 3% by weight, based on the weight of the composition.

Fillers that may be used in the compositions of the invention include, for example, silica powder; talc; polyamide particles and especially those sold under the name Orgasol by the company Atochem; polyethylene powders; microspheres based on acrylic copolymers, such as those based on ethylene glycol dimethacrylate/lauryl methacrylate copolymer sold by the company Dow Corning under the name Polytrap; expanded powders such as hollow microspheres and especially the microspheres sold under the name Expancel by the company Kemanord Plast or under the name Micropearl F 80 ED by the company Matsumoto; powders of natural organic materials such as crosslinked or noncrosslinked corn starch, wheat starch or rice starch, such as the powders of starch crosslinked with octenyl succinate anhydride, sold under the name Dry-Flo by the company National Starch; silicone resin microbeads such as those sold under the name Tospearl by the company Toshiba Silicone; clays (bentone, laponite, saponite, etc.) and mixtures thereof. These fillers may be present in amounts ranging from about 0.1 to about 50% by weight, preferably from 0.5 to about 30% by weight, and more preferably from about 1 to about 20% by weight, based on the weight of the composition.

The compositions of the present invention may further comprise a safe and effective amount of at least one active ingredient or pharmaceutically acceptable salt thereof. The term "safe and effective amount" as used herein, means an amount sufficient to modify the condition to be treated or to deliver the desired skin benefit, while at the same time avoiding serious side effects, at a reasonable benefit to risk ratio within the scope of sound medical judgment. What is a safe and effective amount of the active ingredient will vary with the specific active agent, the ability of the active agent to penetrate through the skin, the age, health and skin condition of the user, and other like factors. Typically, the active ingredient may be present in amounts ranging from about 0.01 to about 20% by weight, preferably from 0.1 to about 10% by weight, and more preferably from about 0.5 to about 5% by weight, based on the weight of the composition.

The active ingredients useful herein can be categorized by their therapeutic benefit or their postulated mode of action. However, it is to be understood that the active ingredients useful herein can in some instances provide more than one therapeutic benefit or operate via more than one mode of action. Therefore, classifications herein are made for the sake of convenience and are not intended to limit the active ingredient to that particular application or applications listed. Also, pharmaceutically acceptable salts of these active ingredients are useful herein. The following active ingredients are useful in the compositions of the present invention.

Anti-Acne Actives: Examples of useful anti-acne actives include the keratolytics such as salicylic acid (o-hydroxybenzoic acid), derivatives of salicylic acid such as 5-octanoyl salicylic acid, and resorcinol; retinoids such as retinoic acid and its derivatives (e.g., cis and trans); sulfur-containing D and L amino acids and their derivatives and salts, particularly their N-acetyl derivatives, a preferred example of which is N-acetyl-L-cysteine; lipoic acid; antibiotics and antimicrobials such as benzoyl peroxide, octopirox, tetracycline, 2,4,4'-trichloro-2'-hydroxy diphenyl ether, 3,4,4'-trichlorobanilide, azelaic acid and its derivatives, phenoxyethanol, phenoxypropanol, phenoxyisopropanol, ethyl acetate, clindamycin and meclocycline; sebostats such as flavonoids; and bile salts such as scymnol sulfate and its derivatives, deoxycholate, and cholate.

Anti-Wrinkle and Anti-Skin Atrophy Actives: Examples of antiwrinkle and anti-skin atrophy actives include retinoic acid and its derivatives (e.g., cis and trans); retinol; retinyl esters; salicylic acid and derivatives thereof; sulfur-containing D and L amino acids and their derivatives and salts, particularly the N-acetyl derivatives, a preferred example of which is N-acetyl-L-cysteine; thiols, e.g. ethane thiol; alpha-hydroxy acids, e.g. glycolic acid, and lactic acid; phytic acid, lipoic acid; lysophosphatidic acid, and skin peel agents (e.g., phenol and the like).

Non-Steroidal Anti-Inflammatory Actives (NSAIDS): Examples of NSAIDS include the following categories: propionic acid derivatives; acetic acid derivatives; fenamic acid derivatives; biphenylcarboxylic acid derivatives; and oxicams. All of these NSAIDS are fully described in U.S. Pat. No. 4,985,459, incorporated by reference herein in its entirety. Examples of useful NSAIDS include acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Also useful are the steroidal anti-inflammatory drugs including hydrocortisone and the like.

Topical Anesthetics: Examples of topical anesthetic drugs include benzocaine, lidocaine, bupivacaine, chlorprocaine, dibucaine, etidocaine, mepivacalne, tetracaine, dyclonine, hexylcaine, procaine, cocaine, ketamine, pramoxine, phenol, and pharmaceutically acceptable salts thereof.

Antimicrobial and Antifungal Actives: Examples of antimicrobial and antifungal actives include .beta.-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate and clotrimazole.

The cosmetic compositions of this invention may also contain sunscreens, which are chemical absorbers that actually absorb harmful ultraviolet radiation. It is well known that chemical absorbers are classified, depending on the type of radiation they protect against, as either UV-A or UV-B absorbers. UV-A absorbers generally absorb radiation in the 320 to 400 nm region of the ultraviolet spectrum. UV-A absorbers include anthranilates, benzophenones, and dibenzoyl methanes. UV-B absorbers generally absorb radiation in the 280 to 320 nm region of the ultraviolet spectrum. UV-B absorbers include p-aminobenzoic acid derivatives, camphor derivatives, cinnamates, and salicylates.

Classifying the chemical absorbers generally as UV-A or UV-B absorbers is accepted within the industry. However, a more precise classification is one based upon the chemical properties of the sunscreens. There are eight major classifications of sunscreen chemical properties, and that are discussed at length in "*Sunscreens—Development, Evaluation and Regulatory Aspects,*" by N. Shaath et al., 2nd. Edition, pages 269-273, Marcel Dekker, Inc. (1997).

The sunscreens useful in the present invention typically comprise chemical absorbers, but may also comprise physical blockers. Exemplary sunscreens which may be formulated into the compositions of the present invention are chemical absorbers such as p-aminobenzoic acid derivatives, anthranilates, benzophenones, camphor derivatives, cinnamic derivatives, dibenzoyl methanes (such as avobenzone also known as Parsol®1789), diphenylacrylate derivatives, salicylic derivatives, triazine derivatives, benzimidazole compounds, bis-benzoazolyl derivatives, methylene bis-(hydroxyphenylbenzotriazole) compounds, the sunscreen polymers and silicones, or mixtures thereof. These are variously described in U.S. Pat. Nos. 2,463,264, 4,367,390, 5,166,355 and 5,237,071 and in EP 863,145, EP 517,104, EP 570,838, EP 796,851, EP 775,698, EP 878,469, EP 933,376, EP 893,119, EP 669,323, GB 2,303,549, DE 1,972,184 and WO 93/04665, the entire contents of which are hereby incorporated by reference. Also exemplary of the sunscreens which may be formulated into the compositions of this invention are physical blockers such as cerium oxides, chromium oxides, cobalt oxides, iron oxides, red petrolatum, silicone-treated titanium dioxide, titanium dioxide, zinc oxide, and/or zirconium oxide, or mixtures thereof.

A wide variety of sunscreens is described in U.S. Pat. Nos. 5,087,445; 5,073,372; and Chapter VIII of *Cosmetics and Science and Technology* (1957) by Segarin et al., pages 189 et seq, the entire contents of each of which are hereby incorporated by reference.

Examples of suitable sunscreens include, but are not limited to: aminobenzoic acid, amyldimethyl PABA, cinoxate, diethanolamine p-methoxycinnamate, digalloyl trioleate, dioxybenzone, 2-ethoxyethyl p-methoxycinnamate, ethyl 4-bis(hydroxypropyl)aminobenzoate, 2-ethylhexyl-2-cyano-3,3-diphenylacrylate, ethylhexyl p-methoxycinnamate, 2-ethylhexyl salicylate, glyceryl aminobenzoate, homomenthyl salicylate, homosalate, 3-imidazol-4-ylacrylic acid and ethyl ester, methyl anthranilate, octyldimethyl PABA, 2-phenylbenzimidazole-5-sulfonic acid and salts, red petrolatum, sulisobenzone, titanium dioxide, triethanolamine salicylate, N,N, N-trimethyl-4-(2-oxoborn-3-ylidene methyl)anillinium methyl sulfate, and mixtures thereof.

Sunscreens active in the UV-A and/or UV-B range can also include, but are not limited to:
p-aminobenzoic acid,
oxyethylene (25 mol) p-aminobenzoate,
2-ethylhexyl p-dimethylaminobenzoate,
ethyl N-oxypropylene p-aminobenzoate,
glycerol p-aminobenzoate,
4-isopropylbenzyl salicylate,
2-ethylhexyl 4-methoxycinnamate,
methyl diisopropylcinnamate,
isoamyl 4-methoxycinnamate,
diethanolamine 4-methoxycinnamate,
3-(4'-trimethylammonium)-benzyliden-bornan-2-one methylsulfate,
2-hydroxy-4-methoxybenzophenone, 2-hydroxy-4-methoxybenzophenone-5-sulfonate,
2,4-dihydroxybenzophenone,
2,2',4,4'-tetrahydroxybenzophenone,
2,2'-dihydroxy-4,4'dimethoxybenzophenone,
2-hydroxy-4-n-octoxybenzophenone,
2-hydroxy-4-methoxy-4'-methoxybenzophenone,
(2-oxoborn-3-ylidene)-tolyl-4-sulfonic acid and soluble salts thereof,
3-(4'-sulfo)benzyliden-bornan-2-one and soluble salts thereof,
3-(4'methylbenzylidene)-d,l-camphor,
3-benzylidene-d,l-camphor,
benzene 1,4-di(3-methylidene-10-camphosulfonic) acid and salts thereof (the product Mexoryl SX described in U.S. Pat. No. 4,585,597,
urocanic acid,
2,4,6-tris[p-(2'-ethylhexyl-1'-oxycarbonyl)-anilino]-1,3,5-triazine,
2-[(p-(tertiobutylamido)anilino]-4,6-bis-[(p-(2'-ethyl-hexyl-1'-oxycarbonyl)anilino]-1,3,5-triazine,
2,4-bis{[4-(2-ethyl-hexyloxy)]-2-hydroxyl-phenyl}-6-(4-methoxy-phenyl)-1,3,5-triazine ("TINOSORB S" marketed by Ciba),
the polymer of N-(2 et 4)-[(2-oxoborn-3-yliden)methyl] benzyl]-acrylamide,
1,4-bisbenzimidazolyl-phenylen-3,3',5,5'-tetrasulfonic acid and salts thereof,
the benzalmalonate-substituted polyorganosiloxanes,
the benzotriazole-substituted polyorganosiloxanes (Drometrizole Trisiloxane),
dispersed 2,2'-methylene-bis-[6-(2H-benzotriazol-2-yl)-4-(1,1,3,3-tetramethylbutyl)phenol] such as that marketed under the trademark MIXXIM BB/100 by Fairmount Chemical, or micronized in dispersed form thereof such as that were marketed under the trademark TINOSORB M by Ciba Specialty Chemicals Corp. (Tarrytown, N.Y.), and
solubilized 2,2'-methylene-bis-[6-(2H-benzotriazol-2-yl)-4-(methyl)phenol] such as that marketed under the trademark MIXXIM BB/200 by Fairmount Chemical.

Typically combinations of one or more of these sunscreens are used.

The dibenzoyl methane derivatives other than avobenzone are described, for example, in FR 2,326,405, FR 2,440,933 and EP 114,607.

Other dibenzoyl methane sunscreens other than avobenzone include (whether singly or in any combination):
2-methyldibenzoylmethane
4-methyldibenzoylmethane
4-isopropyldibenzoylmethane
4-tert-butyldibenzoylmethane
2,4-dimethyldibenzoylmethane
2,5-dimethyldibenzoylmethane
4,4'-diisopropyldibenzoylmethane
4,4'-dimethoxydibenzoylmethane
2-methyl-5-isopropyl-4'-methoxydibenzoylmethane
2-methyl-5-tert-butyl-4'-methoxydibenzoylmethane
2,4-dimethyl-4'-methoxydibenzoylmethane
2,6-dimethyl-4-tert-butyl-4'-methoxydibenzoylmethane Additional sunscreens that can be used are described in pages 2954-2955 of the *International Cosmetic Ingredient Dictionary and Handbook* (9th ed. 2002).

The composition of the invention may be in the form of a makeup product for the skin, in particular an eyeshadow, an eyeliner, a makeup product for the body, a makeup product for the lips such as a lipstick, a lip gloss or a lip pencil optionally having care or treating properties; a makeup product for integuments such as the eyelashes and the hair, in particular a mascara, an eyebrow makeup, or for the nails. The composition of the invention may also be in the form of temporary tattoos. Beyond that, they may be anhydrous in nature or comprise both oil and aqueous phases, in which case, the compositions may form emulsions/suspensions (e.g., oil-in-water, water-in-oil, and multiple emulsions), and are formulated into products such as creams, lotions and gels.

The present invention is further described in terms of the following non-limiting examples. Unless otherwise indicated, all parts and percentages are on a weight-by-weight percentage basis.

EXAMPLES

Lip Compositions

| Phase | Trade Name | Ex. 1 | Ex. 2 | Ex. 3 | Ex. 4 | Ex. 5 |
|---|---|---|---|---|---|---|
| A | Kraton G1657 M | 8.00 | 8.00 | 8.00 | 8.00 | 9.00 |
|   | Regalite R1100 | 24.00 | 24.00 | 24.00 | 24.00 | 27.00 |
|   | Isopropyl palmitate | 16.24 | 26.24 | 16.24 | 16.24 | 16.24 |
|   | Isostearyl palmitate | 8.00 | 0.00 | 8.00 | 4.00 | 4.00 |
|   | DC556 | 4.00 | 0.00 | 2.00 | 8.00 | 4.00 |
|   | Finnsolv TN | 0.00 | 0.00 | 2.00 | 0.00 | 0.00 |
|   | Belsil PDM 1000 | 4.00 | 2.00 | 4.00 | 4.00 | 4.00 |
|   | Puresyn 8 | 10.00 | 12.00 | 10.00 | 10.00 | 10.00 |
|   | Puresyn 150 | 10.00 | 12.00 | 10.00 | 10.00 | 10.00 |
| B | Pigments | 3.63 | 3.63 | 3.63 | 3.63 | 3.63 |
|   | Finnsolv TN | 3.63 | 3.63 | 3.63 | 3.63 | 3.63 |
| C | Fillers | 8.50 | 8.50 | 8.50 | 8.50 | 8.50 |
|   | TOTAL | 100.00 | 100.00 | 100.00 | 100.00 | 100.00 |

All values are expressed in % w/w.

Combine Phase A ingredients together in a beaker, then place the beaker in a 100° C. oil bath and mix with a propeller mixer until the solution is completely uniform. This procedure takes at least 30 minutes.

In a separate beaker combine Phase B ingredients together, then mix by hand until the pigments are totally wet with oil.

Transfer the mixture to a three-roll Mill and mill the color grind until the colors become homogeneous.

Transfer the color grind phase B into the beaker containing phase A.

Add Phase C ingredients into Phase (A+B) mixture and mix for about 5 minutes.

Transfer the resulting fluid to individual packages.

The examples exhibited desirable shine and wear properties.

What is claimed is:

1. A cosmetic composition comprising:
    (a) at least one block copolymer having at least one hard segment and at least one soft segment;
    (b) at least one tackifier component comprising a hydrogenated hydrocarbon resin derived from a styrene/methyl styrene/indene copolymer;
    (c) at least one phenylated silicone;
    (d) at least one solvent selected from the group consisting of long chain and aromatic esters; and
    (e) optionally, at least one colorant,
    wherein the cosmetic composition is a makeup product for the skin, body, lips, eyelashes, hair, eyebrows, or nails, and wherein the at least one block copolymer is present in an amount of from 8% to about 95%, and wherein the at least one hard segment of the at least one block copolymer is styrene.

2. The composition of claim 1 wherein the at least one block copolymer has a hard block with a glass transition temperature $T_g$ of greater than about 50° C, and a soft block with a glass transition temperature $T_g$ of less than about 0° C.

3. The composition according to claim 1 wherein the at least one block copolymer is present in the composition in an amount of from 8% to about 75% by weight, based on the weight of the composition.

4. The composition according to claim 1 wherein the at least one block copolymer is present in the composition in an amount of from 8% to about 50% by weight, based on the weight of the composition.

5. The composition according to claim 1 wherein the at least one block copolymer is present in the composition in an amount of from 8% to about 25% by weight, based on the weight of the composition.

6. The composition of claim 1 wherein the at least one tackifier component is present in the composition in an amount of from greater than 0% to about 95% by weight, based on the weight of the composition.

7. The composition of claim 1 wherein the at least one tackifier component is present in the composition in an amount of from greater than 0% to about 75% by weight, based on the weight of the composition.

8. The composition of claim 1 wherein the at least one tackifier component is present in the composition in an amount of from greater than 0% to about 50% by weight, based on the weight of the composition.

9. The composition of claim 1 wherein the at least one phenylated silicone has an average number molecular weight of less than about 200,000.

10. The composition of claim 1 wherein the at least one phenylated silicone has an average number molecular weight of less than about 80,000.

11. The composition of claim 1 wherein the at least one phenylated silicone has an average number molecular weight of less than about 20,000.

12. The composition of claim 1 wherein the at least one phenylated silicone is present in the composition in an amount of from greater than 0% to about 90% by weight, based on the weight of the composition.

13. The composition of claim 1 wherein the at least one phenylated silicone is present in the composition in an amount of from greater than 0% to about 70% by weight, based on the weight of the composition.

14. The composition of claim 1 wherein the at least one phenylated silicone is present in the composition in an amount of from greater than 0% to about 50% by weight, based on the weight of the composition.

15. The composition of claim 1 wherein the at least one solvent is present in the composition in an amount of from greater than 0% by weight to about 90% by weight, based on the weight of the composition.

16. The composition of claim 1 wherein the tackifier has a solubility parameter corresponding to δ and the block copolymer has at least one segment with a solubility parameter corresponding to δ+2.

17. The composition of claim 1 wherein the composition is a makeup product used to treat lips.

18. A process for treating a keratinous substrate comprising contacting the substrate with a cosmetic composition comprising:
(a) at least one block copolymer having at least one hard segment and at least one soft segment;
(b) at least one tackifier component comprising a hydrogenated hydrocarbon resin derived from a styrene/methyl styrene/indene copolymer;
(c) at least one phenylated silicone;
(d) at least one solvent; and
(e) optionally, at least one colorant,
wherein the cosmetic composition is a makeup product for the skin, body, lips, eyelashes, hair, eyebrows, or nails, and
wherein the at least one block copolymer is present in an amount of from 8% to about 95%, and
wherein the at least one hard segment of the at least one block copolymer is styrene.

19. A cosmetic composition comprising:
(a) from about 1 to about 15% by weight of at least one thermoplastic elastomer chosen from a di-block rubber elastomer and a tri-block rubber elastomer;
(b) from about 1 to about 50% by weight of at least one hydrogenated hydrocarbon resin derived from styrene/methyl styrene/indene copolymers;
(c) from about 0.1% to about 40% by weight of at least one phenylated silicone;
(d) from about 1 to about 50% by weight of at least one solvent;
(e) at least one colorant; and
(f) optionally, at least one wax component, all weights being based on the weight of the composition.

20. The composition of claim 19 wherein the wax component is present in the composition in an amount of from about 0.1% to about 30% by weight, based on the weight of the composition.

21. The composition of claim 19 wherein (b) has a solubility parameter corresponding to δ and (a) has at least one segment with a solubility parameter corresponding to δ+2.

22. The composition of claim 19 wherein the composition is a makeup product used to treat lips.

23. A cosmetic composition comprising:
(a) at least one block copolymer having at least one hard segment and at least one soft segment;
(b) at least one tackifier component comprising a hydrogenated hydrocarbon resin derived from a styrene/methyl styrene/indene copolymer;
(c) at least one phenylated silicone;
(d) at least one solvent; and
(e) optionally, at least one colorant,
wherein the cosmetic composition is a makeup product for the skin, body, lips, eyelashes, hair, eyebrows, or nails, and
wherein the at least one block copolymer is present in an amount of from 8% to about 95%.

* * * * *

UNITED STATES PATENT AND TRADEMARK OFFICE
CERTIFICATE OF CORRECTION

| | | |
|---|---|---|
| PATENT NO. | : 7,884,158 B2 | Page 1 of 2 |
| APPLICATION NO. | : 11/219946 | |
| DATED | : February 8, 2011 | |
| INVENTOR(S) | : Hy Si Bui et al. | |

It is certified that error appears in the above-identified patent and that said Letters Patent is hereby corrected as shown below:

On the Title page, item (75), "François Pradier, Paris, (FR)" should read --François Pradier, New York, NY (US)--.
    Column 1, line 9, "lips nails" should read --lips, nails--.
    Column 1, line 19, "transfer free" should read --transfer-free--.
    Column 2, line 61, "(triblock)." should read --(triblock)).--.
    Column 2, line 66, "is" should read --are--.
    Column 5, line 23, "are identical or different, are each" should read --is identical or different, is--.
    Column 5, line 29, "are identical or different, are each" should read --is identical or different, is--.
    Column 5, line 31, "are" should read --is--.
    Column 5, line 33, "are identical or different, are each" should read --is identical or different, is--.
    Column 5, line 37, "are identical or different, are each" should read --is identical or different, is--.
    Column 5, line 43, "are" should read --is--.
    Column 5, line 55, "are" should read --is--.
    Column 5, line 56, "each be" should read --be--.
    Column 5, line 58, "are identical or different, can, for example, each" should read --is identical or different, can, for example,--.
    Column 5, line 60, "are identical or different, can, for example each be" should read --is identical or different, can, for example, be--.
    Column 5, line 62, "are" should read --is--.
    Column 5, line 63, "each be" should read --be--.
    Column 5, line 65, "are" should read --is--.
    Column 5, line 66, "each be" should read --be--.
    Column 6, line 2, "each be" should read --be--.
    Column 6, line 4, "can each," should read --can,--.
    Column 6, line 6, "can each" should read --can--.

Signed and Sealed this
Twenty-seventh Day of November, 2012

David J. Kappos
*Director of the United States Patent and Trademark Office*

CERTIFICATE OF CORRECTION (continued)
U.S. Pat. No. 7,884,158 B2

Column 8, line 43, "represents" should read --represent--.
Column 13, line 67, "corresponds" should read --correspond--.
Column 24, line 36, "Repeat Unit" should read --repeat Unit--.
Column 25, line 27, "are each" should read --is--.
Column 25, line 38, "are each" should read --is--.
Column 25, line 41, "are each" should read --is--.
Column 25, line 57, "are each" should read --is--.
Column 25, line 60, "are each" should read --is--.
Column 25, line 62, "are each" should read --is--.
Column 26, line 4, "are each" should read --is--.
Column 26, line 7, "are each" should read --is--.
Column 27, line 31, "are each" should read --is--.
Column 27, line 35, "are each" should read --is--.
Column 27, line 64, "are each" should read --is--.
Column 28, line 8, "are each" should read --is--.
Column 28, line 14, "are each" should read --is--.
Column 28, line 19, "are each" should read --is--.
Column 28, line 26, "are each" should read --is--.
Column 28, line 32, "are each" should read --is--.
Column 28, line 45, "is" should read --are--.
Column 41, line 61, "+" should read --±--.
Column 42, line 42, "+" should read --±--.